(12) United States Patent
Cockerill et al.

(10) Patent No.: US 11,078,189 B2
(45) Date of Patent: Aug. 3, 2021

(54) PHARMACEUTICAL COMPOUNDS

(71) Applicant: REVIRAL LIMITED, Stevenage (GB)

(72) Inventors: Stuart George Cockerill, Stevenage (GB); James Good, Stevenage (GB)

(73) Assignee: REVIRAL LIMITED, Stevenage (GB)

( * ) Notice: Subject to any disclaimer, the term of this patent is extended or adjusted under 35 U.S.C. 154(b) by 16 days.

(21) Appl. No.: 16/631,530

(22) PCT Filed: Jul. 20, 2018

(86) PCT No.: PCT/GB2018/052058
§ 371 (c)(1),
(2) Date: Jan. 16, 2020

(87) PCT Pub. No.: WO2019/016566
PCT Pub. Date: Jan. 24, 2019

(65) Prior Publication Data
US 2020/0172515 A1    Jun. 4, 2020

(30) Foreign Application Priority Data

Jul. 20, 2017 (GB) .................................. 1711704

(51) Int. Cl.
| | | |
|---|---|---|
| *C07D 403/06* | (2006.01) | |
| *C07D 413/14* | (2006.01) | |
| *C07D 403/14* | (2006.01) | |
| *C07D 417/14* | (2006.01) | |
| *A61P 11/06* | (2006.01) | |
| *C07D 409/14* | (2006.01) | |

(Continued)

(52) U.S. Cl.
CPC ............ *C07D 403/06* (2013.01); *A61P 11/06* (2018.01); *C07D 401/14* (2013.01); *C07D 403/14* (2013.01); *C07D 409/14* (2013.01); *C07D 413/14* (2013.01); *C07D 417/14* (2013.01); *A61K 45/06* (2013.01)

(58) Field of Classification Search
CPC .. C07D 403/06; C07D 401/14; C07D 403/14; C07D 409/14; C07D 413/14; C07D 417/14; A61P 11/06; A61K 45/06
USPC .................................................... 514/210.16
See application file for complete search history.

(56) References Cited

U.S. PATENT DOCUMENTS

2015/0259367 A1    9/2015    Tahri et al.

FOREIGN PATENT DOCUMENTS

| WO | 2002062290 | 8/2002 |
|---|---|---|
| WO | 2003053344 | 7/2003 |

(Continued)

OTHER PUBLICATIONS

Combrink, et al. Respiratory syncytial virus fusion inhibitors. Part 6: An examination of the effect of structural variation of the benzimidazol-2-one heterocycle moiety. Biorganic & Medicinal Chemistry Letters. 2017. (17): 4784-4790.

(Continued)

*Primary Examiner* — Kristin A Vajda
(74) *Attorney, Agent, or Firm* — Quarles & Brady LLP

(57) ABSTRACT

Benzimidazole derivatives of formula (I): wherein: $R^1$ is —$(CH_2)$m-$R^4$ or $R^2$ is halo, —$(CH_2)_m$—$NH_2$ or —$(CH_2)_n$—C(=NH)—$NH_2$; $R^3$ is H or F; $R^4$ is —NH—$(CH_2)_2$—$(NH)_r$—$R^5$, —NH—$(CHR^5R^6)$ or a group of the following formula (A): (A) W is —$(CH_2)_m$—, —$CH_2$—O—$CH_2$—, —$CH_2$—S—$CH_2$—, —$(CH_2)_r$—$S(O)_2$—$CH_2$— or —$(CH_2)_r$—$NR^5$—$CH_2$—; m is an integer of 1 to 3; n is 1 or 2; p is 1 and V is CH; or p is 0 and V is N; q is 0 or 1; r is 0 or 1; $R^5$ is H, —$SO^2$Me, —$SO_2$Et, —$SO_2CF_3$, —COMe, —$CONMe_2$, —$CONH_2$ or —$CH_2CH_2SO_2$Me; $R^6$ is H or $C_1$-$C_6$ alkyl; and $R^7$ is —$SO_2$Me, —$SO_2$Et, —$SO_2CF_3$, —COMe, —$CONMe_2$, —$CONH_2$ or —$CH_2CH_2SO_2$Me; and the pharmaceutically acceptable salts thereof are inhibitors of RSV and can therefore be used to treat or prevent an RSV infection.

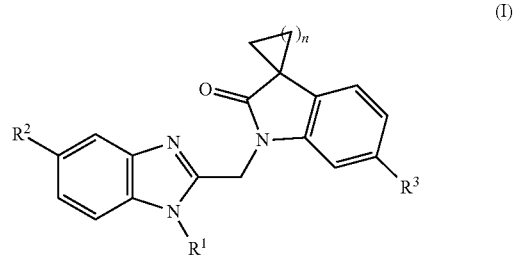

(I)

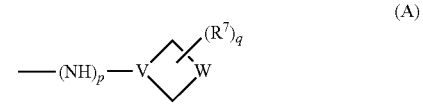

(A)

12 Claims, No Drawings

(51) Int. Cl.
*A61K 45/06* (2006.01)
*C07D 401/14* (2006.01)

(56) References Cited

FOREIGN PATENT DOCUMENTS

| WO | 2010103306 | 9/2010 |
| WO | 2013068769 | 5/2013 |
| WO | 2015022263 | 2/2015 |
| WO | 2016055780 | 4/2016 |

OTHER PUBLICATIONS

PCT.GB2018/052058 International Search Report and Written Opinion. dated Jan. 24, 2019.

PHARMACEUTICAL COMPOUNDS

CROSS-REFERENCE TO RELATED APPLICATIONS

This application represents the national stage entry of PCT International Application No. PCT/GB2018/052058 filed on Jul. 20, 2018, which claims the benefit of Great Britain Patent Application No. 1711704.5 filed on Jul. 20, 2017, the entire contents of which are incorporated herein by reference for all purposes.

FIELD OF THE INVENTION

The present invention relates to benzimidazole compounds and to their use in treating or preventing a respiratory syncytial virus (RSV) infection.

BACKGROUND TO THE INVENTION

RSV is a negative-sense, single-stranded RNA virus of the Paramyxoviridae family. RSV is readily transmitted by secretions from an infected person via surfaces or hand-to-hand transfer. Unlike influenza, it is not transmitted by small-particle aerosols. Following successful inoculation, the incubation period is between four and six days during which time the virus spreads from the nasopharynx to the lower respiratory tract by fusion of infected with uninfected cells and by sloughing of the necrotic epithelium. In infants, coupled with increased mucus secretion and oedema, this can lead to mucus plugging causing hyper-inflation and collapse of distal lung tissue indicative of bronchiolitis. Hypoxia is common and the ability to feed is often impaired because of respiratory distress. In RSV pneumonia, inflammatory infiltration of the airways consists of mononuclear cells and is more generalised, with involvement of the bronchioles, bronchi and alveoli. The duration and degree of viral shedding has been found to correlate with the clinical signs and severity of disease.

RSV is the leading cause of serious respiratory tract infections in infants and young children throughout the world. The highest morbidity and mortality occurs in those born prematurely and for those with chronic lung or heart disease, although many infants hospitalised for RSV infection are otherwise healthy. Severe RSV infection in infancy can lead to several years of recurrent wheezing and is linked to the later development of asthma.

RSV is also a major cause of morbidity and mortality in the elderly and in immunocompromised children and adults as well as those with chronic obstructive pulmonary disease (COPD) and congestive heart failure (CHF).

RSV has a seasonal incidence; it is highly predictable and occurs in the winters of both hemispheres, from September to May in Europe and North America, peaking in December and January, and can occur throughout the year in tropical countries. It affects >90% of infants and young children by the age of two years and as natural immunity is short-lived; many will be re-infected each year. As with influenza, in elderly people, RSV causes around 10% of winter hospitalisations with an associated mortality of 10%.

Current anti-RSV treatment involves the use of a monoclonal antibody to RSV, called palivizumab. Such use of palivizumab is a prophylactic, rather than therapeutic, treatment of RSV. Although this antibody is often effective, its use is restricted to preterm infants and infants at high risk. Indeed, its limited utility means that it is unavailable for many people in need of anti-RSV treatment. There is therefore an urgent need for effective alternatives to existing anti-RSV treatment.

Additionally, several compounds have been proposed as inhibitors of RSV, including benzimidazole-based compounds. For example, K D Combrink et al., Bioorganic & Medicinal Chemistry Letters, 17 (2007), 4784-4790 discloses the compound BMS-433771 and variants thereof. Further benzimidazole-based compounds are disclosed in WO-02/062290, WO-03/053344 and WO-10/103306.

WO 2013/068769 and WO2016/055780 disclose benzimidazole compounds having activity against RSV. However there exists a need to identify further compounds, and in particular compounds having favourable pharmacokinetic profiles.

SUMMARY OF THE INVENTION

It has now been found that a novel series of benzimidazole compounds are active as RSV inhibitors with favourable pharmacokinetics. Accordingly, the present invention provides a compound which is a benzimidazole of formula (I):

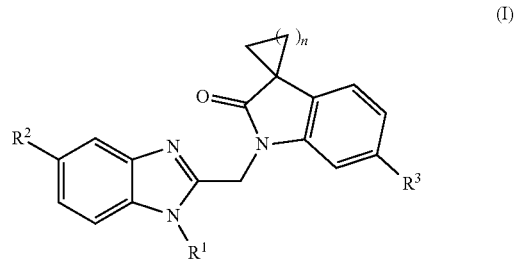

wherein:
$R^1$ is $-(CH_2)_m-R^4$ or

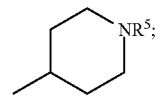

$R^2$ is halo, $-(CH_2)_m-NH_2$ or $-(CH_2)_n-C(=NH)-NH_2$;
$R^3$ is H or F;
$R^4$ is $-NH-(CH_2)_2-(NH)_r-R^5$, $-NH-(CHR^5R^6)$ or a group of the following formula (A):

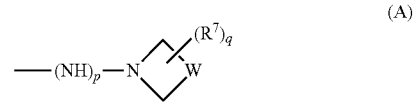

W is $-(CH_2)_m-$, $-CH_2-O-CH_2-$, $-CH_2-S-CH_2-$, $-(CH_2)_r-S(O)_2-CH_2-$ or $-(CH_2)_r-NR^5-CH_2-$;
m is an integer of 1 to 3;
n is 1 or 2;
p is 1 and V is CH; or p is 0 and V is N;
q is 0 or 1;
r is 0 or 1;
$R^5$ is H, $-SO_2Me$, $-SO_2Et$, $-SO_2CF_3$, $-COMe$, $-CONMe_2$, $-CONH_2$ or $-CH_2CH_2SO_2Me$;
$R^6$ is H or $C_1$-$C_6$ alkyl; and $R^7$ is —$SO_2Me$, —$SO_2Et$, —$SO_2CF_3$, —COMe, —$CONMe_2$, —$CONH_2$ or —$CH_2CH_2SO_2Me$;
or a pharmaceutically acceptable salt thereof.

DETAILED DESCRIPTION OF THE INVENTION

When any group, ring, substituent or moiety defined herein is substituted, it is typically substituted by Q as defined below.

A $C_{1-6}$ alkyl group or moiety is linear or branched. A $C_{1-6}$ alkyl group is typically a $C_{1-4}$ alkyl group, or a $C_{4-6}$ alkyl group. Examples of $C_{1-6}$ alkyl groups and moieties include methyl, ethyl, n-propyl, i-propyl, n-butyl, i-butyl, t-butyl, n-pentyl, i-pentyl (i.e. 3-methylbut-1-yl), t-pentyl (i.e. 2-methylbut-2-yl), neopentyl (i.e. 2,2-dimethylpropan-1-yl), n-hexyl, i-hexyl (i.e. 4-methylpentan-1-yl), t-hexyl (i.e. 3-methylpentan-3-yl) and neopentyl (i.e. 3,3-dimethylbutan-1-yl). For the avoidance of doubt, where two alkyl moieties are present in a group, the alkyl moieties may be the same or different. A $C_{1-6}$ alkyl group is unsubstituted or substituted, typically by one or more groups Q as defined below. For example, a $C_{1-6}$ alkyl group is unsubstituted or substituted by 1, 2 or 3 groups Q as defined below.

Q is halo, nitro, —CN, OH, $C_{1-6}$ alkoxy, $C_{1-6}$ hydroxyalkyl, $C_{1-6}$ alkylthio, $C_{1-6}$ haloalkyl, $C_{1-4}$ haloalkoxy, —$CO_2R'''$, —$NR'''_2$, —$SR'''$, —$S(=O)R'''$, —$S(=O)_2R'''$, $C_3$-$C_{10}$ cycloalkyl, 5 to 10-membered heterocyclyl, 5- to 12-membered aryl or 5- to 12-membered heteroaryl, wherein each $R'''$ is independently selected from H, $C_{1-6}$ alkyl, $C_{3-10}$ cycloalkyl, 5 to 10-membered heterocyclyl, 5- to 12-membered aryl and 5- to 12-membered heteroaryl.

A $C_{1-6}$ alkoxy group is linear or branched. It is typically a $C_{1-4}$ alkoxy group, for example a methoxy, ethoxy, propoxy, i-propoxy, n-propoxy, n-butoxy, sec-butoxy or tert-butoxy group. A $C_{1-6}$ alkoxy group is unsubstituted or substituted, typically by one or more groups Q as defined.

A $C_{1-6}$ alkylthio group is linear or branched. It is typically a $C_{1-4}$ alkylthio group, for example a methylthio, ethylthio, propylthio, i-propylthio, n-propylthio, n-butylthio, sec-butylthio or tert-butylthio group. A $C_{1-6}$ alkyltho group is unsubstituted or substituted, typically by one or more groups Q as defined above.

A halogen or halo group is F, Cl, Br or I. Preferably it is F or Cl. A $C_{1-6}$ alkyl group substituted by halogen may be denoted "$C_{1-6}$ haloalkyl", which means a $C_{1-6}$ alkyl group as defined above in which one or more hydrogens is replaced by halo. Likewise a $C_{1-6}$ alkoxy group substituted by halogen may be denoted "$C_{1-6}$ haloalkoxy", which means a $C_{1-6}$ alkoxy group as defined above in which one or more hydrogens is replaced by halo. Typically, $C_{1-6}$ haloalkyl or $C_{1-6}$ haloalkoxy is substituted by 1, 2 or 3 said halogen atoms. Haloalkyl and haloalkoxy groups include perhaloalkyl and perhaloalkoxy groups such as —$CX_3$ and —$OCX_3$ wherein X is a halogen, for example —$CF_3$—$CCl_3$—$OCF_3$ and —$OCCl_3$.

A $C_{1-6}$ hydroxyalkyl group is a $C_{1-6}$ alkyl group as defined above, substituted by one or more OH groups. Typically, it is substituted by one, two or three OH groups. Preferably, it is substituted by a single OH group.

A 5- to 12-membered aryl group is an aromatic carbocyclic group containing from 5 to 12 carbon atoms, for instance from 6 to 10 carbon atoms, such as 6 or 10 carbon atoms. It is monocyclic or a fused bicyclic ring system in which an aromatic ring is fused to another aromatic carbocyclic ring. Examples of a 5- to 12-membered aryl group include phenyl and naphthyl. When substituted, an aryl group is typically substituted by $C_{1-4}$ alkyl or a group Q as defined above, for instance by 1, 2 or 3, groups selected from a $C_{1-4}$ alkyl group and a group Q as defined above.

A $C_{3-10}$ cycloalkyl group is a saturated hydrocarbon ring having from 3 to 10 carbon atoms. A $C_{3-10}$ cycloalkyl group may be, for instance, $C_3$-$C_7$ cycloalkyl such as cyclopropyl, cyclobutyl, cyclopentyl, cyclohexyl, or cycloheptyl. Typically it is $C_3$-$C_6$ cycloalkyl, or $C_4$-$C_6$ cycloalkyl, for example cyclobutyl, cyclopentyl or cyclohexyl. In one embodiment it is cyclobutyl. A $C_{3-10}$ cycloalkyl group is unsubstituted or substituted, typically by one or more groups Q as defined above.

A 5- to 12-membered heteroaryl group or moiety is a 5- to 12-membered aromatic heterocyclic group which contains 1, 2, 3, or 4 heteroatoms selected from O, N and S. It is monocyclic or bicyclic. Typically it contains one N atom and 0, 1, 2 or 3 additional heteroatoms selected from O, S and N. It may be, for example, a 5- to 7-membered heteroaryl group, for instance a 5- or 6-membered N-containing heteroaryl group. Examples include pyridyl, pyrazinyl, pyrimidinyl, pyridazinyl, furanyl, thienyl, pyrazolidinyl, pyrrolyl, oxadiazolyl, oxazolyl, isoxazolyl, thiazolyl, thiadiazolyl, imidazolyl and pyrazolyl groups. Furanyl, thienyl, pyridyl and pyrimidyl groups are preferred. When substituted, a heteroaryl group is typically substituted by one or more, e.g. 1, 2 or 3, groups selected from $C_{1-4}$ alkyl and a group Q as defined above.

A 5- to 10-membered heterocyclyl moiety is a monocyclic or bicyclic non-aromatic, saturated or unsaturated $C_{5-10}$ carbocyclic ring, in which at least one, for example 1, 2 or 3, carbon atoms in the ring are replaced with an atom or group selected from O, S, SO, $SO_2$, CO and N. Typically, it is a saturated $C_{5-10}$ ring in which 1, 2 or 3 of the carbon atoms in the ring are replaced with an atom or group selected from O, S, $SO_2$, CO and NH. More typically it is a monocyclic ring, preferably a monocyclic $C_5$-$C_6$ ring. Examples include piperidyl, piperidin-2,6-dionyl, piperidin-2-onyl, piperazinyl, morpholinyl, thiomorpholinyl, S,S-dioxothiomorpholinyl, 1,3-dioxolanyl, pyrrolidinyl, imidazol-2-onyl, pyrrolidin-2-onyl, tetrahydrofuranyl and tetrahydropyranyl moieties.

For the avoidance of doubt, although the above definitions of heteroaryl and heterocyclyl groups refer to an "N" atom which can be present in the ring, as will be evident to a skilled chemist the N atom will be protonated (or will carry a substituent as defined above) if it is attached to each of the adjacent ring atoms via a single bond. Such protonated forms are embraced within the present definitions of heteroaryl and heterocyclyl groups.

In one embodiment of the benzimidazoles of formula (I), $R^1$ is —$(CH_2)_m$—$R^4$ in which m is 2 or 3 and $R^4$ is —NH—$(CH_2)_2$—$(NH)_r$—$R^5$ wherein r is 0 or 1 and $R^5$ is selected from —$SO_2Me$, —$SO_2Et$ and —$SO_2CF_3$.

In a further embodiment $R^1$ is —$(CH_2)_m$—$R^4$ in which m is 2 or 3 and $R^4$ is —NH—$(CHR^5R^6)$ wherein $R^5$ is —$CONH_2$ or —$CONMe_2$ and $R^6$ is $C_1$-$C_6$ alkyl.

In another embodiment $R^1$ is —$(CH_2)_m$—$R^4$ in which m is 2 or 3 and $R^4$ is —$(CH_2)_m$—$R^4$ in which m is 2 or 3 and $R^4$ is a group of formula (A) in which p is 1, q is 0, V is CH and W is —$(CH_2)_r$—$S(O)_2$—$CH_2$— or —$(CH_2)_r$—$NR^5$—$CH_2$— in which r is 0 and $R^5$ is —$SO_2Me$ or —$SO_2Et$.

In a yet further embodiment $R^1$ is —$(CH_2)_m$—$R^4$ in which m is 2 or 3 and $R^4$ is —$(CH_2)_m$—$R^4$ in which m is 2 or 3 and $R^4$ is a group of formula (A) in which p is 0, V is N, W is —$(CH_2)_m$— in which m is an integer of 1 to 3, q is 1 and $R^5$ is —$SO_2Me$, —$SO_2Et$, —$CONH_2$ or —$CONMe_2$.

In another embodiment R$^1$ is —(CH$_2$)$_m$—R$^4$ in which m is 2 or 3 and R$^4$ is —(CH$_2$)$_m$—R$^4$ in which m is 2 or 3 and R$^4$ is a group of formula (A) in which p is 0, V is N, q is 0 and W is —CH$_2$—O—CH$_2$—, —CH$_2$—S—CH$_2$—, —(CH$_2$)$_r$—S(O)$_2$—CH$_2$— or —(CH$_2$)$_r$—NR$^5$—CH$_2$— in which r is 0 or 1 and R$^5$ is —SO$_2$Me, —SO$_2$Et or —COMe.

Alternatively, R$^1$ is

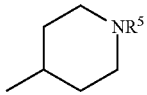

in which R$^5$ is H, —SO$_2$Me, —SO$_2$Et, —COMe, —CONMe$_2$ or —CH$_2$CH$_2$SO$_2$Me.

When in formula (I) R$^4$ is a group of formula (A) and q is 1, the ring substituent R$^7$ may be bonded to any available ring carbon atom.

When W in formula (A) is —(CH$_2$)$_r$—NR$^5$—CH$_2$—, q is typically 0.

Examples of the group of formula (A) include the following structures:

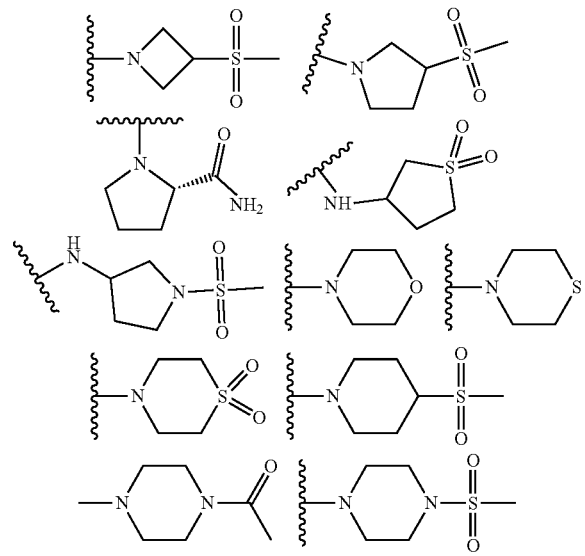

Group R$^2$ in formula (I) is typically F, Cl or —CH$_2$NH$_2$.

Specific compounds of the invention include the following:

1'-({5-Chloro-1-[3-(4-methanesulfonylpiperazin-1-yl)propyl]-1H-1,3-benzodiazol-2-yl}methyl)-6'-fluoro-1',2'-dihydrospiro[cyclopropane-1,3'-indole]-2'-one;

1'-[(5-chloro-1-{2-[(2-methanesulfonylethyl)amino]ethyl}-1H-1,3-benzodiazol-2-yl)methyl]-6'-fluoro-1',2'-dihydrospiro[cyclopropane-1,3'-indole]-2'-one;

N-[2-({2-[5-chloro-2-({6'-fluoro-2'-oxo-1',2'-dihydrospiro[cyclopropane-1,3'-indol]-1'-yl}methyl)-1H-1,3-benzodiazol-1-yl]ethyl}amino)ethyl]1,1,1-trifluoromethanesulfonamide;

3-({2-[5-chloro-2-({6'-fluoro-2'-oxo-1',2'-dihydrospiro[cyclopropane-1,3'-indol]-1'-yl}methyl)-1H-1,3-benzodiazol-1-yl]ethyl}amino)-1λ6-thiolane-1,1-dione;

1'-[(5-chloro-1-{2-[(1-methanesulfonylpyrrolidin-3-yl)amino]ethyl}-1H-1,3-benzodiazol-2-yl)methyl]-6'-fluoro-1',2'-dihydrospiro[cyclopropane-1,3'-indole]-2'-one;

1-{2-[5-chloro-2-({6'-fluoro-2'-oxo-1',2'-dihydrospiro[cyclopropane-1,3'-indol]-1'-yl}methyl)-1H-1,3-benzodiazol-1-yl]ethyl}pyrrolidine-2-carboxamide;

1'-({5-chloro-1-[2-(3-methanesulfonylpyrrolidin-1-yl)ethyl]-1H-1,3-benzodiazol-2-yl}methyl)6'-fluoro-1',2'-dihydrospiro[cyclopropane-1,3'-indole]-2'-one;

1'-({5-chloro-1-[2-(4-methanesulfonylpiperidin-1-yl)ethyl]-1H-1,3-benzodiazol-2-yl}methyl)-6'-fluoro-1',2'-dihydrospiro[cyclopropane-1,3'-indole]-2'-one;

1'-({5-chloro-1-[2-(4-methanesulfonylpiperazin-1-yl)ethyl]-1H-1,3-benzodiazol-2-yl}methyl)-6'-fluoro-1',2'-dihydrospiro[cyclopropan-1,3'-indole]-2'-one;

1'-[(5-Chloro-1-{3-[(2-methanesulfonylethyl)amino]propyl}-1H-1,3-benzodiazol-2-yl)methyl]-6'-fluoro-1',2'-dihydrospiro[cyclopropane-1,3'-indole]-2'-one;

1'-{[5-Chloro-1-(3-{[2-(ethanesulfonyl)ethyl]amino}propyl)-1H-1,3-benzodiazol-2-yl]methyl}-6'-fluoro-1',2'-dihydrospiro[cyclopropane-1,3'-indole]-2'-one;

(2S)-2-({3-[5-chloro-2-({6'-fluoro-2'-oxo-1',2'-dihydrospiro[cyclopropane-1,3'-indol]-1'-yl}methyl)-1H-1,3-benzodiazol-1-yl]propyl}amino)-3-methylbutanamide;

1'-({5-Chloro-1-[3-(3-methanesulfonylazetidin-1-yl)propyl]-1H-1,3-benzodiazol-2-yl}methyl)-6'-fluoro-1',2'-dihydrospiro[cyclopropane-1,3'-indole]-2'-one;

1'-({5-Chloro-1-[3-(3-methanesulfonylpyrrolidin-1-yl)propyl]-1H-1,3-benzodiazol-2-yl}methyl)-6'-fluoro-1',2'-dihydrospiro[cyclopropane-1,3'-indole]-2'-one;

(2S)-1-{3-[5-chloro-2-({6'-fluoro-2'-oxo-1',2'-dihydrospiro[cyclopropane-1,3'-indol]-1'-yl}methyl)-1H-1,3-benzodiazol-1-yl]propyl}pyrrolidine-2-carboxamide;

3-({3-[5-Chloro-2-({6'-fluoro-2'-oxo-1',2'-dihydrospiro[cyclopropane-1,3'-indol]-1'-yl}methyl)-1H-1,3-benzodiazol-1-yl]propyl}amino)-1λ6-thiolane-1,1-dione;

1'-[(5-Chloro-1-{3-[(1-methanesulfonylpyrrolidin-3-yl)amino]propyl}-1H-1,3-benzodiazol-2-yl)methyl]-6'-fluoro-1',2'-dihydrospiro[cyclopropane-1,3'-indole]-2'-one;

1'-({5-Chloro-1-[3-(morpholin-4-yl)propyl]-1H-1,3-benzodiazol-2-yl}methyl)-6'-fluoro-1',2'-dihydrospiro[cyclopropane-1,3'-indole]-2'-one;

1'-({5-Chloro-1-[3-(thiomorpholin-4-yl)propyl]-1H-1,3-benzodiazol-2-yl}methyl)-6'-fluoro-1',2'-dihydrospiro[cyclopropane-1,3'-indole]-2'-one;

4-{3-[5-Chloro-2-({6'-fluoro-2'-oxo-1',2'-dihydrospiro[cyclopropane-1,3'-indol]-1'-yl}methyl)-1H-1,3-benzodiazol-1-yl]propyl}-1λ6-thiomorpholine-1,1-dione;

1'-({5-Chloro-1-[3-(4-methanesulfonylpiperidin-1-yl)propyl]-1H-1,3-benzodiazol-2-yl}methyl)-6'-fluoro-1',2'-dihydrospiro[cyclopropane-1,3'-indole]-2'-one;

1'-({1-[3-(4-Acetylpiperazin-1-yl)propyl]-5-chloro-1H-1,3-benzodiazol-2-yl}methyl)-6'-fluoro-1',2'-dihydrospiro[cyclopropane-1,3'-indole]-2'-one;

6'-Fluoro-1'-[(5-fluoro-1-{3-[(2-methanesulfonylethyl)amino]propyl}-1H-1,3-benzodiazol-2-yl)methyl]-1',2'-dihydrospiro[cyclopropane-1,3'-indole]-2'-one;

(2S)-2-({3-[5-Fluoro-2-({6'-fluoro-2'-oxo-1',2'-dihydrospiro[cyclopropane-1,3'-indol]-1'-yl}methyl)-1H-1,3-benzodiazol-1-yl]propyl}amino)-3-methylbutanamide;

(2S)-1-{3-[5-Fluoro-2-({6'-fluoro-2'-oxo-1',2'-dihydrospiro[cyclopropane-1,3'-indol]-1'-yl}methyl)-1H-1,3-benzodiazol-1-yl]propyl}pyrrolidine-2-carboxamide;

6'-Fluoro-1'-({5-fluoro-1-[3-(morpholin-4-yl)propyl]-1H-1,3-benzodiazol-2-yl}methyl)-1',2'-dihydrospiro[cyclopropane-1,3'-indole]-2'-one;

1'-({1-[3-(4-Acetylpiperazin-1-yl)propyl]-5-fluoro-1H-1,3-benzodiazol-2-yl}methyl)-6'-fluoro-1',2'-dihydrospiro[cyclopropane-1,3'-indole]-2'-one;
6'-Fluoro-1'-({5-fluoro-1-[3-(4-methanesulfonylpiperazin-1-yl)propyl]-1H-1,3-benzodiazol-2-yl}methyl)-1',2'-dihydrospiro[cyclopropane-1,3'-indole]-2'-one;
1'-{[5-Chloro-1-(piperidin-4-yl)-1H-1,3-benzodiazol-2-yl]methyl}-6'-fluoro-1',2'-dihydrospiro[cyclopropane-1,3'-indole]-2'-one;
1'-{[5-Chloro-1-(piperidin-4-yl)-1H-1,3-benzodiazol-2-yl]methyl}-6'-fluoro-1',2'-dihydrospiro[cyclobutane-1,3'-indole]-2'-one;
1'-{[1-(1-Acetylpiperidin-4-yl)-5-chloro-1H-1,3-benzodiazol-2-yl]methyl}-6'-fluoro-1',2'-dihydrospiro[cyclopropane-1,3'-indole]-2'-one;
4-[5-Chloro-2-({6'-fluoro-2'-oxo-1',2'-dihydrospiro[cyclopropane-1,3'-indole]-1'-yl}methyl)-1H-1,3-benzodiazol-1-yl]-N,N-dimethylpiperidine-1-carboxamide;
1'-{[5-Chloro-1-(1-methanesulfonylpiperidin-4-yl)-1H-1,3-benzodiazol-2-yl]methyl}-6'-fluoro-1',2'-dihydrospiro[cyclopropane-1,3'-indole]-2'-one;
1'-{[5-Chloro-1-(1-methanesulfonylpiperidin-4-yl)-1H-1,3-benzodiazol-2-yl]methyl}-6'-fluoro-1',2'-dihydrospiro[cyclobutane-1,3'-indole]-2'-one;
1'-({5-Chloro-1-[1-(ethanesulfonyl)piperidin-4-yl]-1H-1,3-benzodiazol-2-yl}methyl)-6'-fluoro-1',2'-dihydrospiro[cyclopropane-1,3'-indole]-2'-one;
1'-({5-Chloro-1-[1-(2-methanesulfonylethyl)piperidin-4-yl]-1H-1,3-benzodiazol-2-yl}methyl)-6'-fluoro-1',2'-dihydrospiro[cyclopropane-1,3'-indole]-2'-one;
and the pharmaceutically acceptable salts thereof.

The compounds of the invention may contain asymmetric or chiral centres, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Compounds of Formula (I) containing one or more chiral centre may be used in enantiomerically or diastereoisomerically pure form, or in the form of a mixture of isomers.

The present invention embraces all geometric and positional isomers of compounds of the invention as defined above. For example, if a compound of the invention incorporates a double bond or a fused ring, the cis- and trans-forms, as well as mixtures thereof, are embraced within the scope of the invention. Both the single positional isomers and mixture of positional isomers are also within the scope of the present invention.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol tautomerizations. Valence tautomers include interconversions by reorganization of some of the bonding electrons.

Compounds of the invention can be prepared by synthetic methods described in the Examples that follow, or by analogy with such methods.

A benzimidazole of formula (I) can be converted into a pharmaceutically acceptable salt thereof, and a salt can be converted into the free compound, by conventional methods. For instance, a benzimidazole of formula (I) can be contacted with a pharmaceutically acceptable acid to form a pharmaceutically acceptable salt. A pharmaceutically acceptable salt is a salt with a pharmaceutically acceptable acid or base.

Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines.

Compounds of the present invention have been found in biological tests to be inhibitors of respiratory syncytial virus (RSV). The compounds are therefore therapeutically useful. Accordingly, the present invention further provides a compound which is a benzimidazole of formula (I), as defined above, or a pharmaceutically acceptable salt thereof, for use in a method of treating the human or animal body by therapy. The invention also provides a compound of the invention as defined above for use in a method treating or preventing an RSV infection. Still further, the present invention provides the use of a compound of the invention as defined above in the manufacture of a medicament for use in treating or preventing an RSV infection. A subject suffering from or susceptible to an RSV infection may thus be treated by a method comprising the administration thereto of a compound of the invention as defined above. The condition of the subject may thereby be improved or ameliorated.

The RSV infection is typically a respiratory tract infection. The RSV infection may be an infection in a child, for instance a child under ten years of age or an infant under two years of age. In one embodiment the invention provides a compound as defined above for use in treating or preventing an RSV infection in paediatric patients. Alternatively the infection may be an infection in a mature or elderly adult, for instance an adult over 60 years of age, an adult over 70 years of age, or an adult over 80 years of age. The invention further provides a compound for use in treating or preventing an RSV infection in geriatric patients.

The RSV infection may be an infection in an immunocompromised individual or an individual suffering from COPD or CHF. In another embodiment, the RSV infection is an infection in a non-compromised individual, for instance an individual who is otherwise healthy.

A compound of the present invention can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection, infusion, or by inhalation or nebulaisation. The compound is preferably given by oral administration.

The dosage depends on a variety of factors including the age, weight and condition of the patient and the route of administration. Daily dosages can vary within wide limits and will be adjusted to the individual requirements in each particular. Typically, however, the dosage adopted for each route of administration when a compound is administered alone to adult humans is 0.0001 to 650 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

A unit dose form such as a tablet or a capsule will usually contain 1-250 mg of active ingredient. For example, a compound of formula (I) could be administered to a human patient at a dose of between 100-250 mg either once a day, twice or three times a day. For example, a compound of formula (I) could be administered to a human patient at a dose of between 100-250 mg either once a day, twice or three times a day.

The compounds of formula (I) and pharmaceutically acceptable salts thereof may be used on their own. Alternatively, they may be administered in the form of a pharmaceutical composition. The present invention therefore also provides a pharmaceutical composition comprising a compound of formula (I) or a pharmaceutically acceptable salt thereof as hereinbefore defined, in association with a pharmaceutically acceptable adjuvant, diluent or carrier. Conventional procedures for the selection and preparation of suitable pharmaceutical formulations are described in, for example, "Pharmaceuticals-The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The compounds of the invention may be administered in a variety of dosage forms. Thus, they can be administered orally, for example as tablets, troches, lozenges, aqueous or oily suspensions, solutions, dispersible powders or granules. The compounds of the invention may also be administered parenterally, whether subcutaneously, intravenously, intramuscularly, intrasternally, transdermally, by infusion techniques or by inhalation or nebulisation. The compounds may also be administered as suppositories.

Solid oral forms of the pharmaceutical composition of the invention may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulfates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride. Further suitable carriers for suspensions include sterile water, hydroxypropylmethyl cellulose (HPMC), polysorbate 80, polyvinylpyrrolidone (PVP), aerosol AOT (i.e. sodium 1,2-bis(2-ethylhexoxycarbonyl)ethanesulphonate), pluronic F127 and/or captisol (i.e. sulfobutylether-beta-cyclodextrin).

The compounds of the invention may, for example, be formulated as aqueous suspensions in a carrier selected from:
(i) 0.5% w/v hydroxypropylmethyl cellulose (HPMC)/0.1% w/v polysorbate 80;
(ii) 0.67% w/v polyvinylpyrrolidone (PVP)/0.33% w/v aerosol AOT (sodium 1,2-bis(2-ethylhexoxycarbonyl)ethanesulphonate);
(iii) 1% w/v pluronic F 127; and
(iv) 0.5% w/v polysorbate 80.

The carriers may be prepared by standard procedures known to those of skill in the art. For example, each of the carriers (i) to (iv) may be prepared by weighing the required amount of excipient into a suitable vessel, adding approximately 80% of the final volume of water and magnetically stirring until a solution is formed. The carrier is then made up to volume with water. The aqueous suspensions of compounds of formula I may be prepared by weighing the required amount of a compound of formula I into a suitable vessel, adding 100% of the required volume of carrier and magnetically stirring.

Solutions for injection or infusion may contain as carrier, for example, sterile water or preferably they may be in the form of sterile, aqueous, isotonic saline solutions.

The compounds of the invention may also be administered in conjunction with other compounds used for the treatment of viral infections. Thus, the invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment or prevention of a viral infection, particularly infection by RSV.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

Suitable therapeutic agents for use in the combination therapies include
(i) RSV nucleocapsid (N)-protein inhibitors;
(ii) other RSV protein inhibitors, such as those that inhibit the phosphoprotein (P) protein and large (L) protein;
(iii) anti-RSV monoclonal antibodies, such as the F-protein antibodies; (iv) immunomodulating toll-like receptor compounds;

(v) other respiratory virus anti-virals, such as anti-influenza and anti-rhinovirus compounds; and/or (vi) anti-inflammatory compounds.

The RSV nucleocapsid (N)-protein plays a pivotal role in viral transcription and replication, mediating the interaction between the genomic RNA and the virally encoded RNA-dependent RNA polymerase. The RSV P- and L-proteins are components of RSV's virally encoded RNA-dependent RNA polymerase.

According to a further aspect of the invention, there is provided a compound of the formula (I) or a pharmaceutically acceptable salt thereof as hereinbefore defined in combination with one or more of the therapeutic agents listed as (i) to (vi) above for use in the treatment of RSV.

The following Examples illustrate the invention. They do not however, limit the invention in any way.

Examples

Reagents were obtained from commercial sources and were used without further purification. All temperatures are in ° C. TLC was performed on aluminium backed silica gel plates with fluorescence indicator at 254 nM (median pore size 60 Å). Flash column chromatography was performed using a Biotage Isolera One system using KP-Sil, Ultra or KP-NH columns. NMR spectra were recorded on a 400 MHz spectrometer at ambient probe temperature (nominal 295K). Chemical shifts (δ) are given in ppm and calibrated by using the residual peak of the solvent as the internal standard (CDCl$_3$, δ$_H$=7.26 ppm, δ$_C$=77.16 ppm; DMSO-d$_6$, δ$_H$=2.50 ppm, δ$_C$=39.52 ppm). Coupling constants are given in Hertz (Hz). LRMS were recorded using an Advion Plate Express expression$^L$ compact mass spectrometer equipped with either an APCI or ESI ion source.

Abbreviations

| | |
|---|---|
| DMF | N,N-Dimethylformamide |
| DMSO | Dimethyl sulfoxide |
| EtOAc | Ethyl acetate |
| EtOH | Ethanol |
| h | Hour(s) |
| iPrOH | Isopropanol |
| m-CPBA | meta-Chloroperoxybenzoic acid |
| MeCN | Acetonitrile |
| MeOH | Methanol |
| MsCl | Methanesulfonyl chloride |
| NEt$_3$ | Triethylamine |
| rt | room temperature |
| TFA | Trifluoroacetic acid |
| THF | Tetrahydrofuran |

Preparatory Examples

1A: 4-Chloro-N-(3,3-diethoxypropyl)-2-nitroaniline

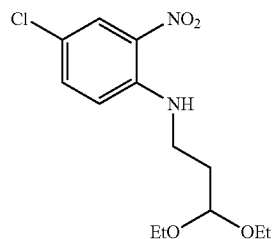 [SMILES: CCOC(CCNc1ccc(Cl)cc1[N+](=O)[O-])OCC]

N,N-Diisopropylethylamine (3.397 mL, 19.5 mmol) followed by 3,3-diethoxypropan-1-amine (3.154 mL, 19.5 mmol) were added to a solution of 4-chloro-1-fluoro-2-nitrobenzene (1.765 mL, 15 mmol), in iPrOH (35 mL) and heated at 80° C. for 4.5 h. After cooling to rt, the reaction mixture was diluted with EtOAc (100 mL) and washed successively with H$_2$O (acidified to ~pH 6 with 0.01 M aqueous HCl, 4×) and brine (1×, 100 mL each), dried (MgSO$_4$) and the solvent removed under reduced pressure to afford the crude product as an orange solid (4.308 g, 97%). $^1$H NMR (400 MHz, CDCl$_3$): δ 8.29 (br s, 1H), 8.17 (d, J=2.6 Hz, 1H), 7.37 (ddd, J=9.2, 2.6, 0.6 Hz, 1H), 6.83 (d, J=9.2 Hz, 1H), 4.65 (t, J=5.0 Hz, 1H), 3.76-3.65 (m, 2H), 3.59-3.49 (m, 2H), 3.44-3.37 (m, 2H), 2.07-2.01 (m, 2H), 1.24 (t, J=7.0 Hz, 6H). LRMS (ESI+) m/z 324.9 [M+Na]$^+$ The following intermediate compounds were prepared by the same general procedure.

| Preparatory Example | Name | $^1$H NMR δ (400 MHz, CDCl$_3$) | LRMS | TLC R$_f$ value |
|---|---|---|---|---|
| 1B | N-(3,3-Diethoxypropyl)-4-fluoro-2-nitroaniline | — | — | 0.66 (EtOAc: petroleum ether 60/40; 1:4) |
| 1C | 4-Chloro-N-(2,2-diethoxyethyl)-2-nitroaniline | 8.19-8.11 (m, 2H), 7.38 (ddd, J = 9.2, 2.6, 0.7 Hz, 1H), 6.85 (d, J = 9.2 Hz, 1H), 4.74 (t, J = 5.6 Hz, 1H), 3.81-3.72 (m, 2H), 3.65-3.55 (m, 2H), 3.43 (t, J = 5.5 Hz, 2H), 1.25 (t, J = 7.0 Hz, 6H) | ESI+ 311.0 [M + Na]$^+$ | — |
| 1D | tert-Butyl 4-[(4-chloro-2-nitrophenyl)amino]piperidine-1-carboxylate | 8.19 (d, J = 2.6 Hz, 1H), 8.06 (d, J = 7.4 Hz, 1H), 7.40-7.35 (m, 1H), 6.84 (d, J = 9.3 Hz, 1H), 4.09-3.95 (m, 2H), 3.69-3.60 (m, 1H), 3.09-2.98 (m, 2H), 2.09-2.00 (m, 2H), 1.57-1.50 (m, 2H), 1.47 (s, 9H) | APCI- 353.9 [M − H]$^-$ | — |

2A: 4-Chloro-N[1]-(3,3-diethoxypropyl)benzene-1,2-diamine

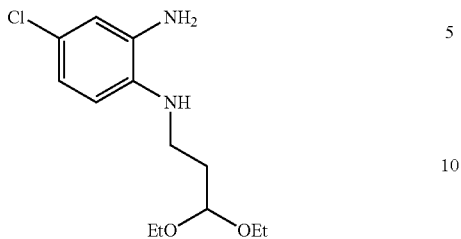

In a 250 mL round-bottom pressure flask 4-chloro-N-(3,3-diethoxypropyl)-2-nitroaniline (intermediate 1A) (4.050 g, 13.38 mmol) was dissolved in EtOH (100 mL) and platinum on carbon (5 wt. % loading, 393 mg) added. The reaction vessel was filled with hydrogen to a pressure of 50 psi and stirred for 3 h. The reaction mixture was filtered through a glass micro fiber filter, washing with EtOH and the solvent removed under reduced pressure. Purification by flash chromatography [$SiO_2$; $CH_2Cl_2/(CH_2Cl_2$:EtOH:$NH_4OH$ 80:20:1); 0-25%] afforded the title compound as a dark brown oil (3.440 g, 94%). $^1$H NMR (400 MHz, $CDCl_3$): δ 6.74 (dd, J=8.4, 2.4 Hz, 1H), 6.67 (d, J=2.4 Hz, 1H), 6.53 (d, J=8.4 Hz, 1H), 4.65 (t, J=5.4 Hz, 1H), 3.83-3.64 (m, 3H), 3.57-3.47 (m, 2H), 3.40 (br s, 2H), 3.17 (t, J=6.4 Hz, 2H), 2.02-1.96 (m, 2H), 1.23 (t, J=7.0 Hz, 6H). LRMS (ESI+) m/z 273.1 [M+Na]$^+$ The following intermediate compounds were prepared by the same general procedure.

| Preparatory Example | Name | $^1$H NMR δ (400 MHz, $CDCl_3$) | LRMS ESI+ | TLC $R_f$ value |
|---|---|---|---|---|
| 2B | N[1]-(3,3-Diethoxypropyl)-4-fluorobenzene-1,2-diamine | — | 279.1 [M + Na]$^+$ | 0.35 (EtOAc: heptane; 1:2) |
| 2C | 4-Chloro-N[1]-(2,2-diethoxyethyl)benzene-1,2-diamine | 6.76 (dd, J = 8.3, 2.3 Hz, 1H), 6.71 (d, J = 2.3 Hz, 1H), 6.58 (d, J = 8.4 Hz, 1H), 4.75 (t, J = 5.4 Hz, 1H), 3.86-3.71 (m, 2H), 3.70-3.54 (m, 3H), 3.48 (s, 2H), 3.22 (d, J = 5.4 Hz, 2H), 1.27 (t, J = 7.0 Hz, 6H). | — | 0.41 (EtOAc: heptane; 1:1) |
| 2D | tert-Butyl 4-[(2-amino-4-chlorophenyl)amino]piperidine-1-carboxylate | 6.75-6.69 (m, 2H), 6.57 (d, J = 8.3 Hz, 1H), 4.03 (br s, 2H), 3.54-3.26 (m, 3H), 3.00-2.86 (m, 2H), 2.04-1.96 (m, 2H), 1.42 (s, 9H), 1.42-1.30 (m, 2H) | 326.3 [M + H]$^+$ | — |

3A: 5-Chloro-2-(chloromethyl)-1-(3,3-diethoxypropyl)-1H-1,3-benzodiazole

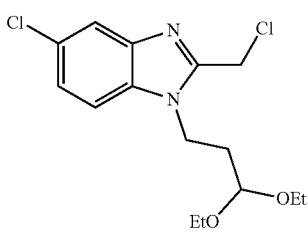 [SMILES: CCOC(CCn1c(CCl)nc2cc(Cl)ccc21)OCC]

A solution of 4-chloro-N[1]-(3,3-diethoxypropyl)benzene-1,2-diamine (intermediate 2A) (2.524 g, 9.27 mmol) and 2-chloro-1,1,1-triethoxyethane (2.499 mL, 18.54 mmol) in EtOH (90 mL) were heated at 75° C. for 7.5 h, then stirred at rt for 12 h. The volatiles were removed under reduced pressure and the reaction mixture purified by flash chromatography ($SiO_2$; EtOAc/petroleum ether 60/80; 0-60%) to give the product as a brown solid (1.537 g, 50%). $^1$H NMR (400 MHz, $CDCl_3$): δ 7.74-7.72 (m, 1H), 7.34-7.26 (m, 2H), 4.87 (s, 2H), 4.48 (t, J=5.0 Hz, 1H), 4.37 (t, J=7.1 Hz, 2H), 3.68-3.58 (m, 2H), 3.49-3.39 (m, 2H), 2.21-2.14 (m, 2H), 1.20 (t, J=7.1 Hz, 6H). LRMS (APCI+) m/z 331.1 [M+H]$^+$ The following intermediate compounds were prepared by the same general procedure.

| Preparatory Example | Name | ¹H NMR δ (400 MHz, CDCl₃) | LRMS AP-CI+ |
|---|---|---|---|
| 3B | 2-(Chloromethyl)-1-(3,3-diethoxypropyl)-5-fluoro-1H-1,3-benzodiazole | 7.42 (dd, J = 9.2, 2.4 Hz, 1H), 7.34-7.30 (m, 1H), 7.08 (td, J = 9.1, 2.4 Hz, 1H), 4.87 (s, 2H), 4.49 (t, J = 5.0 Hz, 1H), 4.37 (t, J = 7.2 Hz, 2H), 3.68-3.59 (m, 2H), 3.49-3.40 (m, 2H), 2.21-2.25 (m, 2H), 1.20 (t, J = 7.1 Hz, 6H) | 314.9 [M + H]⁺ |
| 3C | 5-Chloro-2-(chloromethyl)-1-(2,2-diethoxyethyl)-1H-1,3-benzodiazole | 7.72 (dd, J = 1.9, 0.6 Hz, 1H), 7.35 (dd, J = 8.7, 0.6 Hz, 1H), 7.28 (dd, J = 8.6, 1.9 Hz, 1H), 4.93 (s, 2H), 4.71 (t, J = 5.2 Hz, 1H), 4.36 (d, J = 5.2 Hz, 2H), 3.73 (dq, J = 9.2, 7.0 Hz, 2H), 3.41 (dq, J = 9.2, 7.0 Hz, 2H), 1.12 (t, J = 7.0 Hz, 6H). | 318.1 [M + H]⁺ |
| 3D | tert-Butyl 4-[5-chloro-2-(chloromethyl)-1H-1,3-benzodiazol-1-yl]piperidine-1-carboxylate | 7.73 (d, J = 1.9 Hz, 1H), 7.42 (d, J = 8.7 Hz, 1H), 7.24 (dd, J = 8.8, 2.0 Hz, 1H), 4.85 (s, 2H), 4.52-4.27 (m, 3H), 2.98-2.81 (m, 2H), 2.46-2.31 (m, 2H), 2.03-1.93 (m, 2H), 1.52 (s, 9H) | 383.9 [M + H]⁺ |

4A: 6'-Fluoro-1',2'-dihydrospiro[cyclobutane-1,3'-indole]-2'-one

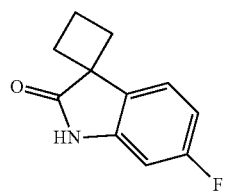 [SMILES: O=C1Nc2cc(F)ccc2C12CCC2]

A dry round-bottomed flask under N₂ was charged with 6-fluoro-2-oxindole (3.00 g, 19.9 mmol), anhydrous THF (60 mL) and diisopropylamine (5.7 mL, 40.7 mmol). The mixture was cooled to 0° C. and n-butyllithium (29.4 mL, 79.4 mmol) added dropwise over 45 min. The mixture was stirred for 2 h at 0° C. before dropwise addition of 1,3-dibromopropane (4.03 mL, 39.7 mmol). The mixture was allowed to attain rt over 1 h and stirred for 20 h at rt. The reaction was quenched with HCl (1 M aq.), and extracted with EtOAc (3×30 mL). The combined organic extracts were washed with water and brine (30 mL each), dried (MgSO₄), and concentrated under reduced pressure. Purification by flash chromatography (0-25% EtOAc:heptane) afforded the product as an orange solid (1.101 g, 29%). ¹H NMR (400 MHz, CDCl₃) δ 8.11 (s, 1H), 7.40 (dd, J=8.2, 5.3 Hz, 1H), 6.75 (ddd, J=9.6, 8.2, 2.3 Hz, 1H), 6.61 (dd, J=8.8, 2.3 Hz, 1H), 2.78-2.58 (m, 2H), 2.46-2.30 (m, 3H), 2.29-2.04 (m, 1H). LRMS (APCI+) m/z 191.9 [M+H]⁺

5A: 1'-{[5-Chloro-1-(3,3-diethoxypropyl)-1H-1,3-benzodiazol-2-yl]methyl}-6'-fluoro-1',2'-dihydrospiro[cyclopropane-1,3'-indole]-2'-one

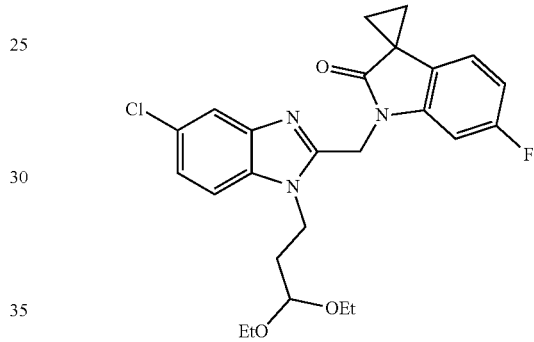

A solution of the alkyl chloride (intermediate 3A) (938 mg, 2.83 mmol), 6'-fluoro-1',2'-dihydrospiro[cyclopropane-1,3'-indole]-2'-one (502 mg, 2.83 mmol) and K₂CO₃ (959 mg, 6.94 mmol) in anhydrous MeCN (18 mL) was heated under an inert atmosphere at 75° C. for 18 h. After cooling to rt, the reaction was diluted with EtOAc (50 mL) and washed with H₂O (2×15 mL). The aqueous layers were extracted with EtOAc (2×25 mL), and the combined organic extracts washed successively with H₂O and brine (50 mL each), dried (MgSO₄) and the solvent removed under reduced pressure. Purification by flash chromatography (SiO₂, EtOAc/petroleum ether 60/80; 8-68%) afforded the product as an off-white solid (1.079 g, 81%). ¹H NMR (400 MHz, CDCl₃): δ 7.77-7.75 (m, 1H), 7.31-7.21 (m, 3H), 6.75-6.65 (m 2H), 5.28 (s, 2H), 4.45 (t, J=5.4 Hz, 1H), 4.35 (t, J=7.3 Hz, 2H), 3.62-3.52 (m, 2H), 3.45-3.35 (m, 2H), 1.97-1.89 (m, 2H), 1.78 (q, J=4.0 Hz, 2H), 1.54 (q, J=4.1 Hz, 1H), 1.16 (t, J=7.1 Hz, 6H). LRMS (APCI+) m/z 471.9 [M+H]⁺

The following compounds were prepared by the same general procedure.

| Preparatory Example | Name | ¹H NMR δ (400 MHz, CDCl₃) | LRMS AP-CI+ |
|---|---|---|---|
| 5B | 1'-{[1-(3,3-Diethoxypropyl)-5-fluoro-1H-1,3-benzodiazol-2-yl]methyl}-6'-fluoro-1',2'- | 7.45 (dd, J = 9.3, 2.4 Hz, 1H), 7.31-7.24 (m, 2H), 7.04 (td, J = 9.1, 2.4 Hz, 1H), 6.75-6.65 (m, 2H), 5.28 (s, 2H), 4.46 (t, J = 5.5 Hz, 1H), 4.36 (t, J = 7.3 Hz, 2H), 3.62-3.55 (m, 2H), | 455.9 [M + H]⁺ |

| Preparatory Example | Name | $^1$H NMR δ (400 MHz, CDCl$_3$) | LRMS AP-CI+ |
|---|---|---|---|
| | dihydrospiro[cyclopropane-1,3'-indole]-2'-one | 3.46-3.36 (m, 2H), 1.97-1.90 (m, 2H), 1.78 (q, J = 4.1 Hz, 2H), 1.53 (q, J = 4.2 Hz, 2H), 1.16 (t, J = 7.1 Hz, 6H) | |
| 5C | 1'-{[5-Chloro-1-(2,2-diethoxyethyl)-1H-1,3-benzodiazol-2-yl]methyl}-6'-fluoro-1',2'-dihydrospiro[cyclopropane-1,3'-indole]-2'-one | 7.75 (dd, J = 2.0, 0.5 Hz, 1H), 7.35-7.30 (m, 1H), 7.29-7.21 (m, 2H), 6.76-6.65 (m, 2H), 5.30 (s, 2H), 4.61 (t, J = 5.2 Hz, 1H), 4.43 (d, J = 5.2 Hz, 2H), 3.62 (dq, J = 9.3, 7.0 Hz, 2H), 3.35 (dq, J = 9.3, 7.0 Hz, 2H), 1.77 (q, J = 4.1 Hz, 2H), 1.53 (q, J = 4.1 Hz, 2H), 1.03 (t, J = 7.0 Hz, 6H). | 458.1 [M + H]$^+$ |
| 5D | tert-Butyl 4-[5-chloro-2-({6'-fluoro-2'-oxo-1',2'-dihydrospiro[cyclopropane-1,3'-indole]-1'-yl}methyl)-1H-1,3-benzodiazol-1-yl]piperidine-1-carboxylate | 7.79 (d, J = 2.0 Hz, 1H), 7.38 (d, J = 8.7 Hz, 1H), 7.28-7.13 (m, 1H), 7.19 (dd, J = 8.7, 2.0 Hz, 1H), 6.74-6.65 (m, 2H), 5.30 (s, 2H), 4.85-4.75 (m, 1H), 4.35-4.26 (m, 2H), 2.94-2.76 (m, 2H), 2.33-2.20 (m, 2H), 1.77-1.73 (m, 2H), 1.57-1.53 (m, 2H), 1.49 (s, 9H) | 524.8 [M + H]$^+$ |
| 5E | tert-Butyl 4-[5-chloro-2-({6'-fluoro-2'-oxo-1',2'-dihydrospiro[cyclobutane-1,3'-indole]-1'-yl}methyl)-1H-1,3-benzodiazol-1-yl] piperidine-1-carboxylate | 7.83 (dd, J = 11.2, 2.0 Hz, 1H), 7.52-7.36 (m, 3H), 7.30-7.27 (m, 1H), 6.77 (ddd, J = 9.3, 8.2, 2.3 Hz, 1H), 5.37 (s, 2H), 5.05-4.87 (m, 1H), 4.35-4.25 (m, 2H), 3.03-2.88 (m, 2H), 2.68-2.59 (m, 2H), 2.43-2.23 (m, 6H), 1.70-1.61 (m, 2H), 1.50 (s, 9H). | 539.8 [M + H]$^+$ |

6A: 3-[5-Chloro-2-({6'-fluoro-2'-oxo-1',2'-dihydrospiro[cyclopropane-1,3'-indole]-1'-yl}methyl)-1H-1,3-benzodiazol-1-yl]propanal

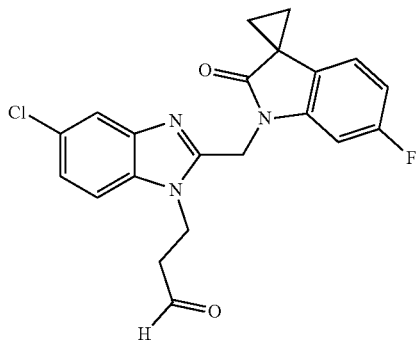 [SMILES: O=CCCn1c(CN2C(=O)C3(CC3)c3ccc(F)cc32)nc2cc(Cl)ccc21]

HCl (2 M aq. solution, 10 mL) was added to a solution of intermediate 5A (1.079 g, 2.29 mmol) in THF (15 mL) and stirred at rt for 16 h. The reaction was quenched with saturated aq. NaHCO$_3$ solution (~25 mL) and extracted with EtOAc (4×50 mL). The combined organic extracts were washed successively with H$_2$O and brine (75 mL each), dried (MgSO$_4$) and the solvent removed under reduced pressure. Purification by flash chromatography (SiO$_2$, 10-100% EtOAc in heptane) afforded the product as an off-white solid (766 mg, 84%). $^1$H NMR (400 MHz, CDCl$_3$): δ 9.69 (s, 1H), 7.67-7.55 (m, 2H), 7.30-7.26 (m, 1H), 7.10-7.04 (m, 2H), 6.85-6.79 (m, 1H), 5.37 (s, 2H), 4.59 (t, J=6.9 Hz, 2H), 3.04 (t, J=6.8 Hz, 2H), 1.72-1.69 (m, 2H), 1.60-1.54 (m, 2H). LRMS (APCI+) m/z 397.8 [M+H]$^+$ The following intermediate compound was prepared by the same general procedure.

| Preparatory Example | Name | $^1$H NMR (400 MHz) | LRMS AP-CI+ |
|---|---|---|---|
| 6B | 3-[5-Fluoro-2-({6'-fluoro-2'-oxo-1',2'-dihydrospiro[cyclopropane-1,3'-indole]-1'-yl}methyl)-1H-1,3-benzodiazol-1-yl]propanal | (DMSO-d$_6$): δ 9.70 (s, 1H), 7.67-7.60 (m, 1H) 7.41 (dd J = 9.8, 2.4 Hz 1H) 7.14-7.04 (m, 3H), 6.85-6.78 (m, 1H), 5.36 (s, 2H), 4.59 (t, J = 6.9 Hz, 2H), 3.04 (t, J = 6.9 Hz, 2H), 1.71-1.67 (m, 2H), 1.59-1.54 (m, 2H) | 382.0 [M + H]$^+$ |

7A: 2-[5-Chloro-2-({6'-fluoro-2'-oxo-1,2'-dihydrospiro[cyclopropane-1,3'-indole]-1'-yl}methyl)-1H-1,3-benzodiazol-1-yl]acetaldehyde

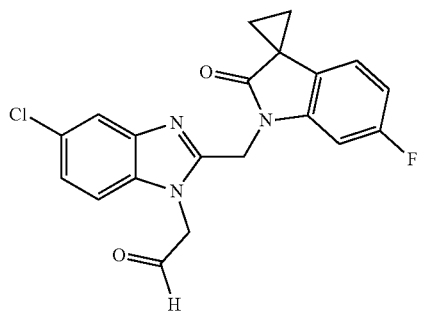 [SMILES: O=CCn1c(CN2C(=O)C3(CC3)c3ccc(F)cc32)nc2cc(Cl)ccc21]

HCl (6 M aqueous solution; 10 mL) was added to a solution of intermediate 5C in anhydrous THF (11 mL) and heated at 60° C. for 5.5 h, and then at 40° C. for a further 16 h. The reaction was quenched with saturated aqueous NaHCO$_3$ solution (25 mL) and extracted with EtOAc (4×50 mL). The combined organic extracts were washed with water and brine (25 mL each), dried (MgSO$_4$), and concentrated under reduced pressure. Purification by flash chromatography (30-70% EtOAc:heptane) afforded an orange solid (430 mg, 64%). $^1$H NMR (400 MHz, CDCl$_3$) δ 9.58 (s, 1H), 7.83 (d, J=1.9 Hz, 1H), 7.39-7.31 (m, 1H), 7.30-7.25 (m, 1H), 7.06 (d, J=8.6 Hz, 1H), 6.73 (dd, J=7.7, 1.6 Hz, 2H), 5.20 (s, 2H), 3.61 (t, J=6.5 Hz, 2H), 1.77-1.71 (m, 2H), 1.59-1.53 (m, 2H). LRMS (APCI+) m/z 384.9 [M+H]$^+$ Examples Reductive Aminations 1. 1'-({5-Chloro-1-[3-(4-methanesulfonylpiperazin-1-yl)propyl]-1H-1,3-benzodiazol-2-yl}methyl)-6'-fluoro-1,2'-dihydrospiro[cyclopropane-1,3'-indole]-2'-one

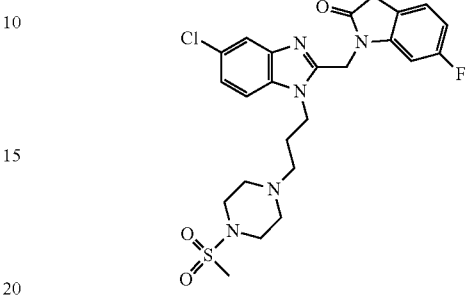

The following general procedure was used for reductive aminations. 1-Methanesulfonylpiperazine (27 mg, 0.166 mmol) was added to a solution of intermediate 6A (60 mg, 0.151 mmol) in 1,2-dichloroethane (2.5 mL) and stirred at rt for 7 h. NaBH(OAc)$_3$ (45 mg, 0.211 mmol) was then added and the reaction stirred for 18 h at rt. The reaction was quenched with NaOH (1 M aqueous solution, 4 mL), extracted with CH$_2$Cl$_2$ (4×10 mL), the combined organic extracts washed with brine (5 mL), dried (Na$_2$SO$_4$) and the solvent removed under reduced pressure. Purification by flash chromatography (SiO$_2$, 100% EtOAc, then 0-5% MeOH in CH$_2$Cl$_2$) afforded the product as a white solid (64 mg, 78%). $^1$H NMR (400 MHz, DMSO-d$_6$): δ 7.69 (d, J=1.9 Hz, 1H), 7.64 (d, J=8.7 Hz, 1H), 7.28 (dd, J=8.6, 2.0 Hz, 1H), 7.14-7.05 (m, 2H), 6.86-6.79 (m, 1H), 5.34 (s, 2H), 4.35 (t, J=6.7 Hz, 2H), 3.09-3.02 (m, 4H), 2.85 (s, 3H), 2.40-2.33 (m, 4H), 2.27 (t, J=6.6 Hz, 1H), 1.90 (p, J=6.4 Hz, 1H), 1.72-1.67 (m, 2H), 1.60-1.55 (m, 2H). LRMS (APCI+) m/z 545.7 [M+H]$^+$ The following compounds of the invention were prepared with intermediate 7A by the general reductive amination procedure described for the compound of Example 1.

TABLE 1

5-Chloro aminoethyl analogues prepared via reductive amination

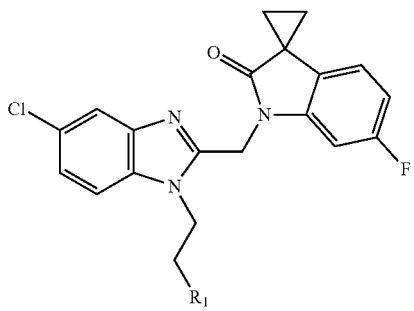

| Example | Name | R$^1$ | $^1$H NMR δ (400 MHz, CDCl$_3$) | LRMS AP-CI+ |
|---|---|---|---|---|
| 2 | 1'-[(5-chloro-1-{2-[(2-methanesulfonylethyl)amino]ethyl}-1H-1,3-benzodiazol-2-yl)methyl]-6'-fluoro-1',2'-dihydrospiro[cyclopropane-1,3'-indole]-2'-one |  | 7.78 (t, J = 1.2 Hz, 1H), 7.31 (dd, J = 9.0, 2.0 Hz, 1H), 7.26-7.23 (m, 2H), 6.77-6.68 (m, 2H), 5.31 (s, 2H), 4.35 (t, J = 6.2 Hz, 2H), 3.08-2.96 (m, 4H), 2.93 (t, J = 6.2 Hz, 2H), 2.81 (s, 3H), 1.77 (q, J = 4.0 Hz, 2H), 1.55 (q, J = 4.0 Hz, 2H). | 491.1 [M + H]$^+$ |

TABLE 1-continued

5-Chloro aminoethyl analogues prepared via reductive amination

| Example | Name | R¹ | ¹H NMR δ (400 MHz, CDCl₃) | LRMS AP-CI+ |
|---|---|---|---|---|
| 3 | N-[2-({2-[5-chloro-2-({6'-fluoro-2'-oxo-1',2'-dihydrospiro[cyclopropane-1,3'-indole]-1'-yl}methyl)-1H-1,3-benzodiazol-1-yl]ethyl}amino)ethyl]1,1,1-trifluoromethanesulfonamide | —NH—CH₂CH₂—NH—SO₂—CF₃ | 7.79 (dd, J =1 .8, 0.7 Hz, 1H), 7.31-7.23 (m, 3H), 6.83-6.67 (m, 3H), 5.43 (s, 2H), 4.35 (t, J = 6.1 Hz, 2H), 3.38-3.29 (m, 2H), 3.02 (q, J = 5.8 Hz, 2H), 2.91-2.77 (m, 2H), 1.81 (q, J = 4.2 Hz, 2H), 1.61 (q, J = 4.2 Hz, 2H). | 560.1 [M + H]⁺ |
| 4 | 3-({2-[5-chloro-2-({6'-fluoro-2'-oxo-1',2'-dihydrospiro[cyclopropane-1,3'-indole]-1'-yl}methyl)-1H-1,3-benzodiazol-1-yl]ethyl}amino)-1λ⁶-thiolane-1,1-dione | (thiolane-1,1-dione-3-yl)NH— | 7.80 (q, J = 1.6 Hz, 1H), 7.41-7.24 (m, 3H), 6.86-6.63 (m, 3H), 5.42-5.29 (m, 2H), 4.37 (t, J = 6.0 Hz, 2H), 3.46 (dt, J = 11.6, 6.5 Hz, 1H), 3.15 (td, J = 13.7, 7.1 Hz, 2H), 3.09-2.87 (m, 4H), 2.72 (dd, J = 13.3, 6.2 Hz, 1H), 2.33-2.16 (m, 1H), 2.02-1.79 (m, 2H), 1.58 (dq, J = 8.4, 4.2 Hz, 3H). | 503.7 [M + H]⁺ |
| 5 | 1'-[(5-chloro-1-{2-[(1-methanesulfonylpyrrolidin-3-yl)amino]ethyl}-1H-1,3-benzodiazol-2-yl)methyl]-6'-fluoro-1',2'-dihydrospiro[cyclopropane-1,3'-indole]-2'-one | (1-methanesulfonylpyrrolidin-3-yl)NH— | 7.78 (t, J = 1.2 Hz, 1H), 7.31 (dd, J = 9.0, 2.2 Hz, 1H), 7.26 (d, J = 1.4 Hz, 2H), 6.78-6.65 (m, 2H), 5.35-5.27 (m, 2H), 4.34 (t, J = 6.0 Hz, 2H), 3.42-3.18 (m, 4H), 2.89 (dt, J = 7.8, 2.7 Hz, 3H), 2.66 (s, 3H), 2.00 (d, J = 7.2 Hz, 1H), 1.77 (q, J = 4.0 Hz, 2H), 1.65-1.50 (m, 4H) | 532.8 [M + H]⁺ |
| 6 | 1-{2-[5-chloro-2-({6'-fluoro-2'-oxo-1',2'-dihydrospiro[cyclopropane-1,3'-indole]-1'-yl}methyl)-1H-1,3-benzodiazol-1-yl]ethyl}pyrrolidine-2-carboxamide | pyrrolidin-1-yl-2-carboxamide | 7.78 (dd, J = 1.8, 0.6 Hz, 1H), 7.37-7.32 (m, 1H), 7.29-7.17 (m, 2H), 6.79-6.69 (m, 2H), 6.62 (s, 1H), 5.41-5.16 (m, 2H), 4.94 (s, 1H), 4.52-4.32 (m, 2H), 3.24 (t, J = 7.9 Hz, 1H), 3.11-2.90 (m, 2H), 2.75 (dt, J = 12.4, 5.8 Hz, 1H), 2.41-2.25 (m, 1H), 2.27-2.11 (m, 1H), 1.91-1.74 (m, 4H), 1.65-1.48 (m, 3H). | 481.8 [M + H]⁺ |
| 7 | 1'-({5-chloro-1-[2-(3-methanesulfonylpyrrolidin-1-yl)ethyl]-1H-1,3-benzodiazol-2-yl}methyl)6'-fluoro-1',2'-dihydrospiro[cyclopropane-1,3'-indole]-2'-one | (3-methanesulfonylpyrrolidin-1-yl)— | 7.78 (t, J = 1.2 Hz, 1H), 7.33 (dd, J = 9.1, 2.1 Hz, 1H), 7.25 (dd, J = 3.2, 1.6 Hz, 2H), 6.77-6.57 (m, 2H), 5.35-5.15 (m, 2H), 4.43-4.34 (m, 2H), 3.54-3.40 (m, 1H), 3.01 (dd, J = 10.5, 5.5 Hz, 1H), 2.95-2.86 (m, 1H), 2.85-2.73 (m, 3H), 2.79 (m, 3H), 2.65 (q, J = 8.3, 7.6 Hz, 1H), 2.31-2.09 (m, 2H), 1.78 (q, J = 3.6 Hz, 2H), 1.55 (q, J = 3.6 Hz, 2H) | 516.7 [M + H]⁺ |

TABLE 1-continued

5-Chloro aminoethyl analogues prepared via reductive amination

| Example | Name | R¹ | ¹H NMR δ (400 MHz, CDCl₃) | LRMS AP-CI+ |
|---|---|---|---|---|
| 8 | 1'-({5-chloro-1-[2-(4-methanesulfonylpiperidin-1-yl)ethyl]-1H-1,3-benzodiazol-2-yl}methyl)-6'-fluoro-1',2'-dihydrospiro[cyclopropane-1,3'-indole]-2'-one | piperidine-N with 4-SO₂CH₃ | 7.81 (dd, J = 1.6, 0.9 Hz, 1H), 7.38 (dd, J = 9.0, 2.1 Hz, 1H), 7.32-7.15 (m, 2H), 6.84-6.68 (m, 2H), 5.32 (s, 2H), 4.40 (t, J = 6.1 Hz, 2H), 3.06 (d, J = 11.7 Hz, 2H), 2.84 (s, 3H), 2.84-2.79 (m, 1H), 2.64 (t, J = 6.1 Hz, 2H), 2.17-2.08 (m, 4H), 1.93-1.77 (m, 4H), 1.55 (q, J = 4.0 Hz, 2H) | 531.8 [M + H]⁺ |
| 9 | 1'-({5-chloro-1-[2-(4-methanesulfonylpiperazin-1-yl)ethyl]-1H-1,3-benzodiazol-2-yl}methyl)-6'-fluoro-1',2'-dihydrospiro[cyclopropan-1,3'-indole]-2'-one | piperazine-N,N'-SO₂CH₃ | 7.78 (dd, J = 1.7, 0.6 Hz, 1H), 7.33 (dd, J = 8.9, 2.1 Hz, 1H), 7.28-7.20 (m, 2H), 6.76-6.68 (m, 2H), 5.30 (s, 2H), 4.38 (t, J = 6.2 Hz, 2H), 3.23-3.15 (m, 4H), 2.76 (s, 3H), 2.66 (t, J = 6.2 Hz, 2H), 2.62-2.56 (m, 4H), 1.77 (q, J = 4.1 Hz, 2H), 1.56-1.50 (m, 2H). | 532.1 [M + H]⁺ |

The following compounds were prepared with intermediate 6A by the general procedure described above for the compound of Example 1.

TABLE 2

5-Chloro aminopropyl examples prepared via reductive amination

| Example | Name | R¹ | ¹H NMR δ (400 MHz, DMSO-d₆) | LRMS AP-CI+ |
|---|---|---|---|---|
| 10 | 1'-[(5-Chloro-1-{3-[(2-methanesulfonylethyl)amino]propyl}-1H-1,3-benzodiazol-2-yl)methyl]-6'-fluoro-1',2'-dihydrospiro[cyclopropane-1,3'-indole]-2'-one | NH-CH₂CH₂-SO₂CH₃ | 7.68 (d, J = 1.9 Hz, 1H), 7.63 (d, J = 8.7 Hz, 1H), 7.27 (dd, J = 8.6, 2.0 Hz, 1H), 7.11-7.05 (m, 2H), 6.86-6.79 (m, 1H), 5.32 (s, 2H), 4.36 (t, J = 7.1 Hz, 2H), 3.22 (t, J = 6.6 Hz, 2H), 3.00 (s, 3H), 2.89 (t, J = 6.5 Hz, 2H), 2.00 (br s, 1H), 1.82 (p, J = 6.9 Hz, 2H), 1.72-1.67 (m, 5H), 1.60-1.55 (m, 2H) | 504.8 [M + H]⁺ |

TABLE 2-continued

5-Chloro aminopropyl examples prepared via reductive amination

[Structure: 5-chloro-benzimidazole linked via methylene to a 6'-fluoro-spiro[cyclopropane-1,3'-indol]-2'-one; the benzimidazole N1 bears a propyl chain terminating in R₁]

| Example | Name | R¹ | ¹H NMR δ (400 MHz, DMSO-d₆) | LRMS AP-CI+ |
|---|---|---|---|---|
| 11 | 1'-{[5-Chloro-1-(3-{2-(ethanesulfonyl)ethyl]amino}propyl)-1H-1,3-benzodiazol-2-yl]methyl}-6'-fluoro-1',2'-dihydrospiro[cyclopropane-1,3'-indole]-2'-one | -NH-CH₂CH₂-S(O)₂-Et | 7.68 (d, J = 1.9 Hz, 1H), 7.63 (d, J = 8.7 Hz, 1H), 7.27 (dd, J = 8.6, 2.0 Hz, 1H), 7.11-7.05 (m, 2H), 6.87-6.79 (m, 1H), 5.32 (s, 2H), 4.39-4 33 (m 2H) 3.20-3.08 (m, 4H), 2.88 (t, J = 6.7 Hz, 2H), 2.08 (br s, 1H), 1.81 (p, J = 6.7 Hz, 2H) 1.72-1.67 (m, 2H), 1.59-1.55 (m, 2H), 1.19 (t, J = 7.4 Hz, 3H). | 519.1 [M + H]⁺ |
| 12 | (2S)-2-({3-[5-chloro-2-({6'-fluoro-2'-oxo-1',2'-dihydrospiro[cyclopropane-1,3'-indole]-1'-yl}methyl)-1H-1,3-benzodiazol-1-yl]propyl}amino)-3-methylbutanamide | -NH-CH(iPr)-C(O)NH₂ | 7.68 (d, J = 1.9 Hz, 1H), 7.63 (d, J = 8.6 Hz, 1H), 7.34-7.30 (m, 1H), 7.26 (dd, J = 8.6, 2.0 Hz, 1H), 7.11-7.04 (m, 2H), 6.99 (d, J = 1.9 Hz, 1H), 6.86-6.77 (m, 1H), 5.38-5.28 (m, 2H), 4.41-4.35 (m, 2H), 2.65-2.58 (m, 1H), 2.34-2.25 (m, 1H), 1.88-1.67 (m, 6H), 1.60-1.55 (m, 2H), 0.93-0.86 (m, 6H) | 497.7 [M + H]⁺ |
| 13 | 1'-({5-Chloro-1-[3-(3-methanesulfonylazetidin-1-yl)propyl]-1H-1,3-benzodiazol-2-yl}methyl)-6'-fluoro-1',2'-dihydrospiro[cyclopropane-1,3'-indole]-2'-one | N-azetidinyl-3-S(O)₂Me | 7.67 (d, J = 1.9 Hz, 1H), 7.63 (d, J = 8.7 Hz, 1H), 7.27 (dd, J = 8.6, 2.0 Hz, 1H), 7.11-7.05 (m, 2H), 6.86-6.79 (m, 1H), 5.34 (s, 2H), 4.32 (t, J = 6.9 Hz, 2H), 4.11 (p, J = 7.1 Hz, 1H), 3.47 (t, J = 8.1 Hz, 2H), 3.33-3.28 (m, 2H), 2.95 (s, 3H), 2.36-2.31 (m, 2H), 1.75-1.67 (m, 4H), 1.57-1.53 (m, 2H) | 516.8 [M + H]⁺ |
| 14 | 1'-({5-Chloro-1-[3-(3-methanesulfonylpyrrolidin-1-yl)propyl]-1H-1,3-benzodiazol-2-yl}methyl)-6'-fluoro-1',2'-dihydrospiro[cyclopropane-1,3'-indole]-2'-one | N-pyrrolidinyl-3-S(O)₂Me | 7.68 (d, J = 1.9 Hz, 1H), 7.65 (d, J = 8.7 Hz, 1H), 7.26 (dd, J = 8.6, 2.0 Hz, 1H), 7.12-7.05 (m, 2H), 6.85-6.79 (m, 1H), 5.37-5.28 (m, 2H), 4.38-4.32 (m, 2H), 3.82-3.74 (m, 1H), 2.93 (s, 3H), 2.84-2.74 (m, 2H), 2.35-2.30 (m, 2H), 2.12-2.05 (m, 2H), 1.93-1.85 (m, 2H), 1.71-1.67 (m, 2H), 1.60-1.55 (m, 2H) | 530.8 [M + H]⁺ |
| 15 | (2S)-1-{3-[5-chloro-2-({6'-fluoro-2'-oxo-1',2'-dihydrospiro[cyclopropane-1,3'-indole]-1'-yl}methyl)-1H-1,3-benzodiazol-1-yl]propyl}pyrrolidine-2-carboxamide | N-pyrrolidinyl-2-C(O)NH₂ | 7.69 (d, J = 1.9 Hz, 1H), 7.65 (d, J = 8.7 Hz, 1H), 7.71-7.61 (m, 2H), 7.30-7.22 (m, 2H), 7.13-7.03 (m, 3H), 6.86-6.78 (m, 1H), 5.37-5.26 (m, 2H), 4.51-4.41 (m, 1H), 4.35-4.25 (m, 1H), 3.12-3.05 (m, 1H), 2.83-2.77 (m, 1H), 2.64-2.55 (m, 1H), 2.41-2.32 (m, 1H), 2.23-2.15 (m, 1H), 2.05-1.96 (m, 1H), 1.89-1.78 (m, 2H), 1.76-1.63 (m, 5H), 1.61-1.54 (m, 2H) | 495.9 [M + H]⁺ |
| 16 | 3-({3-[5-Chloro-2-({6'-fluoro-2'-oxo-1',2'-dihydrospiro[cyclopropane-1,3'-indole]-1'-yl}methyl)-1H-1,3-benzodiazol-1-yl]propyl}amino)-1λ6-thiolane-1,1-dione | -NH-(thiolane-3-yl-1,1-dione) | 7.68 (d, J = 2.0 Hz, 1H), 7.63 (d, J = 8.7 Hz, 1H), 7.28 (dd, J = 8.6, 2.0 Hz, 1H), 7.12-7.05 (m, 2H), 6.86-6.79 (m, 1H), 5.32 (s, 2H), 4.36 (t, J = 7.3 Hz, 2H), 3.27-3.18 (m, 1H), 3.07-2.98 (m, 1H), 2.80 (dd, J = 12.9, 6.6 Hz, 1H), 2.31-2.21 (m, 2H), 1.96-1.77 (m, 3H), 1.72-1.67 (m, 2H), 1.60-1.55 (m, 2H) | 517.2 [M + H]⁺ |

TABLE 2-continued

5-Chloro aminopropyl examples prepared via reductive amination

| Example | Name | R¹ | ¹H NMR δ (400 MHz, DMSO-d₆) | LRMS AP-CI+ |
|---|---|---|---|---|
| 17 | 1'-[(5-Chloro-1-{3-[(1-methanesulfonylpyrrolidin-3-yl)amino]propyl}-1H-1,3-benzodiazol-2-yl)methyl]-6'-fluoro-1',2'-dihydrospiro[cyclopropane-1,3'-indole]-2'-one | (pyrrolidin-3-ylamino with N-SO₂ group) | 7.69 (d, J = 1.9 Hz, 1H), 7.63 (d, J = 8.7 Hz, 1H), 7.28 (dd, J = 8.6, 2.0 Hz, 1H), 7.11-7.05 (m, 2H), 6.86-6.79 (m, 1H), 5.32 (s, 2H), 4.37 (t, J = 7.3 Hz, 2H), 3.23-3.16 (m, 1H), 2.97 (dd, J = 10.2, 4.6 Hz, 1H), 2.86 (s, 3H), 2.00-1.90 (m, 2H), 1.86-1.77 (m, 2H), 1.73-1.61 (m, 3H), 1.60-1.55 (m, 2H) | 546.3 [M + H]⁺ |
| 18 | 1'-({5-Chloro-1-[3-(morpholin-4-yl)propyl]-1H-1,3-benzodiazol-2-yl}methyl)-6'-fluoro-1',2'-dihydrospiro[cyclopropane-1,3'-indole]-2'-one | morpholin-4-yl | 7.68 (d, J = 1.9 Hz, 1H), 7.63 (d, J = 8.7 Hz, 1H), 7.27 (dd, J = 8.6, 2.0 Hz, 1H), 7.13-7.04 (m, 2H), 6.85-6.78 (m, 1H), 5.36 (s, 2H), 4.36 (t, J = 6.8 Hz, 2H), 3.57-3.50 (m, 4H), 2.29-2.22 (m, 4H), 2.19 (t, J = 6.6 Hz, 2H), 1.94-1.84 (m, 2H), 1.71-1.66 (m, 2H), 1.59-1.55 (m, 2H) | 468.9 [M + H]⁺ |
| 19 | 1'-({5-Chloro-1-[3-(thiomorpholin-4-yl)propyl]-1H-1,3-benzodiazol-2-yl}methyl)-6'-fluoro-1',2'-dihydrospiro[cyclopropane-1,3'-indole]-2'-one | thiomorpholin-4-yl | 7.69 (d, J = 1.9 Hz, 1H), 7.62 (d, J = 8.6 Hz, 1H), 7.27 (dd, J = 8.6, 2.0 Hz, 1H), 7.13-7.05 (m, 3H), 6.85-6.79 (m, 1H), 5.34 (s, 2H), 4.34 (t, J = 6.8 Hz, 2H), 2.58-2.52 (m, 8H), 2.23 (t, J = 6.6 Hz, 2H), 1.88 (p, J = 6.7 Hz, 2H), 1.72-1.67 (m, 2H), 1.60-1.55 (m, 2H) | 484.8 [M + H]⁺ |
| 20 | 1'-({5-Chloro-1-[3-(4-methanesulfonylpiperidin-1-yl)propyl]-1H-1,3-benzodiazol-2-yl}methyl)-6'-fluoro-1',2'-dihydrospiro[cyclopropane-1,3'-indole]-2'-one | 4-methanesulfonylpiperidin-1-yl | 7.69 (d, J = 2.0 Hz, 1H), 7.62 (d, J = 8.7 Hz, 1H), 7.27 (dd, J = 8.7, 2.0 Hz, 1H), 7.13-7.05 (m, 2H), 6.85-6.80 (m, 1H), 5.34 (s, 2H), 4.35 (t, J = 6.9 Hz, 2H), 3.05-2.96 (m, 1H), 2.94-2.87 (m, 5H), 2.21 (t, J = 6.6 Hz, 2H), 1.97-1.79 (m, 6H), 1.72-1.67 (m, 2H), 1.65-1.53 (m, 4H) | 544.8 [M + H]⁺ |
| 21 | 1'-({1-[3-(4-Acetylpiperazin-1-yl)propyl]-5-chloro-1H-1,3-benzodiazol-2-yl}methyl)-6'-fluoro-1',2'-dihydrospiro[cyclopropane-1,3'-indole]-2'-one | 4-acetylpiperazin-1-yl | 7.69 (d, J = 1.9 Hz, 1H), 7.64 (d, J = 8.7 Hz, 1H), 7.27 (dd, J = 8.6, 2.0 Hz, 1H), 7.13-7.05 (m, 3H), 6.86-6.79 (m, 1H), 5.36 (s, 2H), 4.37 (t, J = 6.7 Hz, 2H), 3.41-3.35 (m, 4H), 2.29-2.19 (m, 6H), 1.96 (s, 3H), 1.94-1.86 (m, 2H), 1.72-1.66 (m, 2H), 1.60-1.55 (m, 2H) | 509.9 [M + H]⁺ |

The following compounds were prepared with intermediate 6B by the general reductive amination procedure described for Example 1.

TABLE 3

5-Fluoro aminopropyl analogues prepared via reductive amination

| Example | Name | R¹ | $^{1}$H NMR δ (400 MHz, DMSO-d$_6$) | LRMS AP-Cl+ |
|---|---|---|---|---|
| 22 | 6'-Fluoro-1'-[(5-fluoro-1-{3-[(2-methanesulfonylethyl)amino]propyl}-1H-1,3-benzodiazol-2-yl)methyl]-1',2'-dihydrospiro[cyclopropane-1,3'-indole]-2'-one | | 7.60 (dd, J = 8.9, 4.8 Hz, 1H), 7.43 (dd, J = 9.8, 2.4 Hz, 1H), 7.15-7.04 (m, 3H), 6.86-6.79 (m, 1H), 5.31 (s, 2H), 4.36 (t, J = 7.2 Hz, 2H), 3.22 (t, J = 6.7 Hz, 2H), 3.01 (s, 3H), 2.89 (t, J = 6.7 Hz, 2H), 2.08-1.98 (m, 1H), 2.02 (br s, 1H), 1.82 (p, J = 6.9 Hz. 2H), 1.72-1.67 (m, 5H), 1.60-1.55 (m, 2H) | 488.8 [M + H]⁺ |
| 23 | (2S)-2-({3-[5-Fluoro-2-({6'-fluoro-2'-oxo-1',2'-dihydrospiro[cyclopropane-1,3'-indole]-1'-yl}methyl)-1H-1,3-benzodiazol-1-yl]propyl}amino)-3-methylbutanamide | | 7.60 (dd, J = 8.9, 4.8 Hz, 1H), 7.42 (dd, J = 9.8, 2.4 Hz, 1H), 7.32 (d, J = 2.2 Hz, 1H), 7.14-7.04 (m, 3H), 6.99 (d, J = 2.0 Hz, 1H), 6.85-6.79 (m, 1H), 5.37-5.26 (m, 2H), 4.42-4.33 (m, 2H), 2.66-2.59 (m, 1H), 2.34-2.26 (m, 1H), 1.91-1.66 (m, 6H), 1.60-1.55 (m, 2H), 0.93-0.86 (m, 6H) | 481.9 [M + H]⁺ |
| 24 | (2S)-1-{3-[5-Fluoro-2-({6'-fluoro-2'-oxo-1',2'-dihydrospiro[cyclopropane-1,3'-indole]-1'-yl}methyl)-1H-1,3-benzodiazol-1-yl]propyl}pyrrolidine-2-carboxamide | | 7.62 (dd, J = 8.9, 4.7 Hz, 1H), 7.43 (dd, J = 9.8, 2.4 Hz, 1H), 7.26-7.21 (m, 1H), 7.15-7.02 (m, 4H), 6.86-6.78 (m, 1H), 5.35-5.21 (m, 2H), 4.50-4.40 (m, 1H), 4.34-4.24 (m, 1H), 3.12-3.05 (m, 1H), 2.83-2.78 (m, 1H), 2.64-2.55 (m, 1H), 2.41-2.35 (m, 1H), 2.19 (q, J =8.2 Hz, 1H), 2.05-1.96 (m, 1H), 1.89-1.77 (m, 2H), 1.74-1.67 (m, 5H), 1.61-1.55 (m, 2H) | 479.8 [M + H]⁺ |
| 25 | 6'-Fluoro-1'-({5-fluoro-1-[3-(morpholin-4-yl)propyl]-1H-1,3-benzodiazol-2-yl}methyl)-1',2'-dihydrospiro[cyclopropane-1,3'-indole]-2'-one | | 7.63-7.55 (m, 1H), 7.46-7.40 (m, 1H), 7.15-7.04 (m, 3H), 6.86-6.77 (m, 1H), 5.33 (s, 2H), 4.36 (t, J = 6.8 Hz, 2H), 3.57-3.37 (m, 4H), 2.34-2.15 (m, 6H), 1.93-1.83 (m, 2H), 1.71-1.66 (m, 2H), 1.59-1.55 (m, 2H) | 453.3 [M + H]⁺ |
| 26 | 1'-({1-[3-(4-Acetylpiperazin-1-yl)propyl]-5-fluoro-1H-1,3-benzodiazol-2-yl}methyl)-6'-fluoro-1',2'-dihydrospiro[cyclopropane-1,3'-indole]-2'-one | | 7.61 (dd, J = 8.9, 4.7 Hz, 1H), 7.43 (dd, J = 9.8, 2.4 Hz, 1H), 7.15-7.05 (m, 3H), 6.86-6.79 (m, 1H), 5.35 (s, 2H), 4.37 (t, J = 6.8 Hz, 2H), 3.42-3.39 (m, 4H), 2.30-2.18 (m, 6H), 1.96 (s, 3H), 1.94-1.86 (m, 2H), 1.72-1.67 (m, 2H), 1.60-1.55 (m, 2H) | 493.9 [M + H]⁺ |
| 27 | 6'-Fluoro-1'-({5-fluoro-1-[3-(4-methanesulfonylpiperazin-1-yl)propyl]-1H-1,3-benzodiazol-2-yl}methyl)-1',2'-dihydrospiro[cyclopropane-1,3'-indole]-2'-one | | 7.61 (dd, J = 8.9, 4.7 Hz, 1H), 7.43 (dd, J = 9.8, 2.4 Hz, 1H), 7.16-7.05 (m, 3H), 6.86-6.79 (m, 1H), 5.35 (s, 2H), 4.35 (t, J = 6.9 Hz, 2H), 3.09-3.04 (m, 4H), 2.85 (s, 3H), 2.41-2.35 (m, 4H), 2.30-2.25 (m, 2H), 1.90 (p, J = 6.7 Hz, 1H), 1.72-1.66 (m, 2H), 1.60-1.55 (m, 2H) | 530.0 [M + H]⁺ |

28: 4-{3-[5-Chloro-2-({6'-fluoro-2'-oxo-1',2'-dihydrospiro[cyclopropane-1,3'-indole]-1'-yl}methyl)-1H-1,3-benzodiazol-1- yl]propyl}-1λ⁶-thiomorpholine-1,1-dione

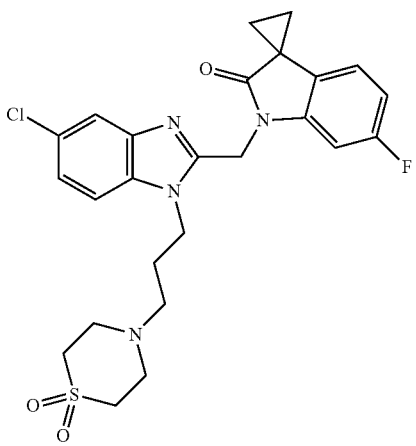 [SMILES: O=C1N(Cc2nc3cc(Cl)ccc3n2CCCN2CCS(=O)(=O)CC2)c2cc(F)ccc2C12CC2]

m-CPBA (~77% pure, 155 mg, 0.691 mmol) was added to a cooled (0° C.) solution of compound 19 (112 mg, 0.231 mmol) in CH$_2$Cl$_2$ (5 mL) and stirred at rt for 5.5 h. The reaction was diluted with CH$_2$Cl$_2$ (10 mL) and washed with saturated aqueous NaHCO$_3$ solution (3×15 mL). The combined aqueous washings were extracted with CH$_2$Cl$_2$ (2×10 mL). The combined organic extracts were washed with saturated aqueous NaHCO$_3$ solution (3×15 mL), dried (Na$_2$SO$_4$) and the solvent removed under reduced pressure. Purification by flash chromatography (SiO$_2$, 0-20% MeOH in CH$_2$Cl$_2$ with 1% NH$_4$OH) gave a white solid (43 mg, 36%). $^1$H NMR (400 MHz, DMSO-d$_6$): δ 7.71-7.69 (m, 2H), 7.28 (dd, J=8.6, 2.1 Hz, 1H), 7.13 (dd, J=9.6, 2.4 Hz, 1H), 7.08 (dd, J=8.2, 5.4 Hz, 1H), 6.85-6.79 (m, 1H), 5.37 (s, 2H), 4.54 (t, J=7.3 Hz, 2H), 3.96-3.86 (m, 2H), 3.83-3.74 (m, 2H), 3.41-3.35 (m, 4H), 3.23-3.15 (m, 2H). 2.25 (p, J=7.0 Hz, 2H), 1.72-1.67 (m, 2H), 1.60-1.55 (m, 2H). LRMS (APCI+) m/z 534.2 [M+NH$_4$]$^+$ 29: 1'-{[5-Chloro-1-(piperidin-4-yl)-1H-1,3-benzodiazol-2-yl]methyl}-6'-fluoro-1',2'-dihydrospiro[cyclopropane-1,3'-indole]-2'- one

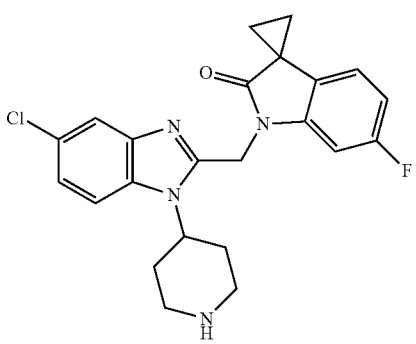 [SMILES: O=C1N(Cc2nc3cc(Cl)ccc3n2C2CCNCC2)c2cc(F)ccc2C12CC2]

A solution of intermediate 5D (725 mg, 1.38 mmol) in trifluoroacetic acid (TFA; 2.59 mL) and CH$_2$Cl$_2$ (8 mL) was stirred at rt for 5 h. The volatiles were removed under reduced pressure, the residue partitioned between saturated aqueous NaHCO$_3$ solution (20 mL) and CH$_2$Cl$_2$ (20 mL) and separated. The aqueous layer was extracted with CH$_2$Cl$_2$ (3×20 mL), the combined organic extracts washed with brine (10 mL), dried (Na$_2$SO$_4$) and the solvent removed under reduced pressure. Purification by flash chromatography [0-100% EtOH:CH$_2$Cl$_2$:NH$_4$OH (50:8:1) in CH$_2$Cl$_2$] afforded a pale brown solid (584 mg, 99%). $^1$H NMR (400 MHz, DMSO-d$_6$): δ 7.79 (d, J=8.8 Hz, 1H), 7.73 (d, J=2.1 Hz, 1H), 7.26 (dd, J=8.8, 2.1 Hz, 1H), 7.11-7.04 (m, 2H), 6.84-6.78 (m, 1H), 5.36 (s, 2H), 4.67-4.57 (m, 1H), 4.36 (br s, 1H), 3.16-3.09 (m, 2H), 2.65-2.56 (m, 2H), 2.30-2.17 (m, 2H), 1.72-1.64 (m, 4H), 1.58-1.55 (m, 2H). LRMS (APCI+) m/z 424.8 [M+H]$^+$ 30: 1'-{[5-Chloro-1-(piperidin-4-yl)-1H-1,3-benzodiazol-2-yl]methyl}-6'-fluoro-1',2'-dihydrospiro[cyclobutane-1,3'-indole]-2'- one

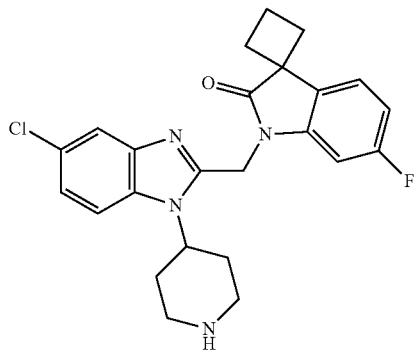 [SMILES: O=C1N(Cc2nc3cc(Cl)ccc3n2C2CCNCC2)c2cc(F)ccc2C12CCC2]

Prepared by an analogous procedure to that described for compound 29 from intermediate 5E. LRMS (APCI+) m/z 439.9 [M+H]$^+$. R$_f$ 0.02 EtOH:CH$_2$Cl$_2$:NH$_4$OH (100:8:1).

31: 1'-{[1-(1-Acetylpiperidin-4-yl)-5-chloro-1H-1,3-benzodiazol-2-yl]methyl}-6'-fluoro-1',2'-dihydrospiro[cyclopropane-1,3'-indole]-2'-one

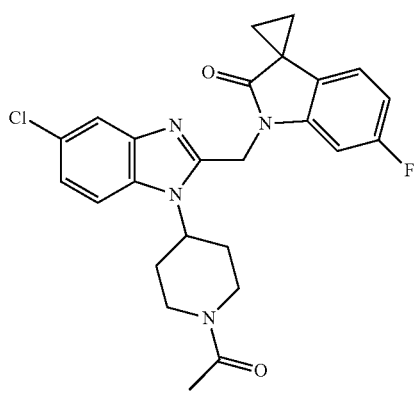 [SMILES: CC(=O)N1CCC(n2c(CN3C(=O)C4(CC4)c4ccc(F)cc43)nc3cc(Cl)ccc32)CC1]

Acetyl chloride (20.1 µL, 0.280 mmol) was added to a cooled (0° C.) solution of compound 29 (60 mg, 0.140 mmol) and NEt₃ (43.3 µL, 0.310 mmol) in anhydrous CH₂Cl₂ (2.5 mL) under N₂ and stirred at rt for 17 h. The reaction was diluted with CH₂Cl₂ (20 mL), washed with water and brine (10 mL each), dried (MgSO₄) and the solvent removed under reduced pressure. Purification by flash chromatography (0-5% EtOH in CH₂Cl₂) afforded a pale brown solid (36 mg, 54%). ¹H NMR (400 MHz, DMSO-d₆): δ 7.75-7.70 (m, 2H), 7.20 (dd, J=8.7, 2.1 Hz, 1H), 7.12-7.05 (m, 2H), 6.85-6.79 (m, 1H), 5.40 (s, 2H), 4.83-4.74 (m, 1H), 4.65-4.58 (m, 1H), 4.06-3.98 (m, 1H), 3.19-3.10 (m, 1H), 2.65-2.54 (m, 1H), 2.39-2.27 (m, 1H), 2.16-2.03 (m, 4H), 1.86-1.75 (m, 2H), 1.72-1.68 (m, 2H), 1.60-1.55 (m, 2H). LRMS (APCI+) m/z 466.8 [M+H]⁺

32: 4-[5-Chloro-2-({6'-fluoro-2'-oxo-1',2'-dihydrospiro[cyclopropane-1,3'-indole]-1'-yl}methyl)-1H-1,3-benzodiazol-1-yl]-N,N-dimethylpiperidine-1carboxamide

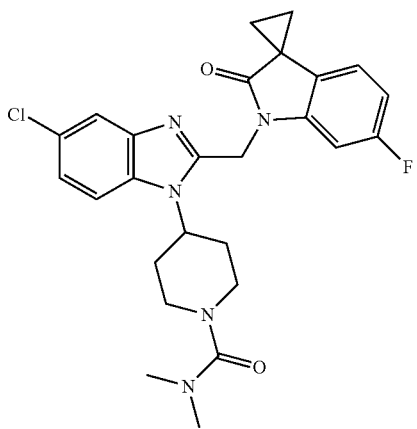 [SMILES: CN(C)C(=O)N1CCC(n2c(CN3C(=O)C4(CC4)c4ccc(F)cc43)nc3cc(Cl)ccc32)CC1]

N,N-dimethylcarbamoyl chloride (19.5 µL, 0.210 mmol) was added to a cooled (0° C.) solution of compound 29 (60 mg, 0.140 mmol) and NEt₃ (30.5 µL, 0.219 mmol) in anhydrous CH₂Cl₂ (2.5 mL) under N₂ and stirred at rt for 17 h. The reaction was quenched with saturated aqueous NH₄Cl solution (10 mL) and extracted with CH₂Cl₂ (10 mL). The organic extracts were washed with water and brine (10 mL each), dried (MgSO₄) and the solvent removed under reduced pressure. Purification by flash chromatography (0-10% EtOH in CH₂Cl₂) afforded a pale brown solid (70 mg, 69%). ¹H NMR (400 MHz, DMSO-d₆): δ 7.73 (d, J=2.0 Hz, 1H), 7.64 (d, J=8.8 Hz, 1H), 7.24 (dd, J=8.7, 2.1 Hz, 1H), 7.12-7.05 (m, 2H), 6.85-6.79 (m, 1H), 5.39 (s, 2H), 4.75-4.67 (m, 1H), 3.73-3.66 (m, 2H), 2.86-2.76 (m, 8H), 2.31-2.21 (m, 2H), 1.80-1.72 (m, 2H), 1.73-1.68 (m, 2H), 1.59-1.55 (m, 2H). LRMS (APCI+) m/z 495.8 [M+H]⁺

33: 1'-{[5-Chloro-1-(1-methanesulfonylpiperidin-4-yl)-1H-1,3-benzodiazol-2-yl]methyl}-6'-fluoro-1',2'-dihydrospiro[cyclopropane-1,3'-indole]-2'-one

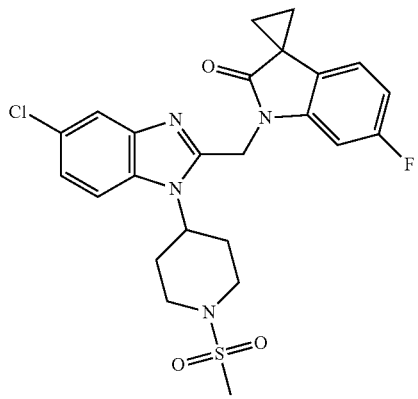 [SMILES: CS(=O)(=O)N1CCC(n2c(CN3C(=O)C4(CC4)c4ccc(F)cc43)nc3cc(Cl)ccc32)CC1]

Methanesulfonyl chloride (MsCl, 13.1 µL, 0.170 mmol) was added to a cooled (0° C.) solution of compound 29 (60 mg, 0.140 mmol) and NEt₃ (24.6 µL, 0.180 mmol) in anhydrous CH₂Cl₂ (2.5 mL) under N₂ and stirred at rt for 17 h. Extra MsCl (8.7 µL, 0.113 mmol) and NEt₃ (15.8 µL, 0.113 mmol) were added and the reaction stirred for a further 4.5 h. The reaction was diluted with CH₂Cl₂ (20 mL), washed with water and brine (10 mL each), dried (MgSO₄) and the solvent removed under reduced pressure. Purification by flash chromatography [50-100% EtOAc in heptane, then 0-10% EtOH:CH₂Cl₂:NH₄OH (50:8:1) in CH₂Cl₂] afforded a white solid (49 mg, 69%). ¹H NMR (400 MHz, DMSO-d₆): δ 7.72 (d, J=2.0 Hz, 1H), 7.70 (d, J=8.8 Hz, 1H), 7.23 (dd, J=8.7, 2.1 Hz, 1H), 7.14-7.05 (m, 2H), 6.85-6.79 (m, 1H), 5.39 (s, 2H), 4.78-4.68 (m, 1H), 3.83-3.76 (m, 2H), 3.00 (s, 3H), 2.92-2.84 (m, 2H), 2.40-2.34 (m, 2H), 1.95-1.89 (m, 2H), 1.73-1.68 (m, 2H), 1.61-1.56 (m, 2H). LRMS (APCI+) m/z 502.8 [M+H]⁺

34: 1'-{[5-Chloro-1-(1-methanesulfonylpiperidin-4-yl)-1H-1,3-benzodiazol-2-yl]methyl}-6'-fluoro-1',2'-dihydrospiro[cyclobutane-1,3'-indole]-2'-one

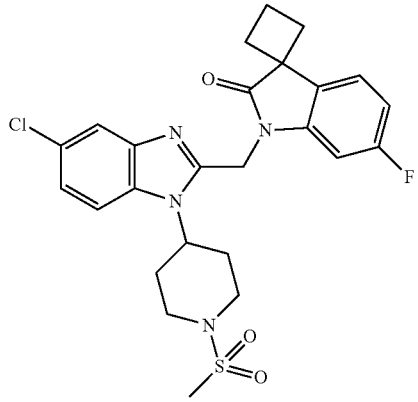 [SMILES: CS(=O)(=O)N1CCC(n2c(CN3C(=O)C4(CCC4)c4ccc(F)cc43)nc3cc(Cl)ccc32)CC1]

Prepared by an analogous procedure to that described for compound 33 from compound 30. ¹H NMR (400 MHz, DMSO-d₆) δ 7.74-7.59 (m, 3H), 7.23 (dd, J=8.8, 2.1 Hz, 1H), 7.06 (dd, J=9.6, 2.4 Hz, 1H), 6.88 (ddd, J=10.4, 8.2, 2.4 Hz, 1H), 5.28 (s, 2H), 4.75 (t, J=12.4 Hz, 1H), 3.81 (d, J=11.8 Hz, 2H), 3.02 (s, 3H), 2.89 (s, 2H), 2.41-2.31 (m, 4H), 2.25 (q, J=7.4 Hz, 2H), 1.91 (d, J=12.3 Hz, 2H). LRMS (APCI+) m/z 517.9 [M+H]⁺

35: 1'-({5-Chloro-1-[1-(ethanesulfonyl)piperidin-4-yl]-1H-1,3-benzodiazol-2-yl}methyl)-6'-fluoro-1',2'-dihydrospiro[cyclopropane-1,3'-indole]-2'-one

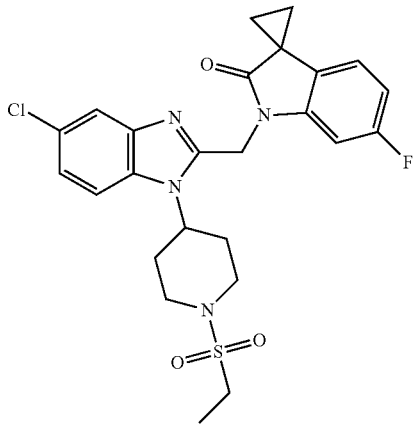 [SMILES: CCS(=O)(=O)N1CCC(n2c(CN3C(=O)C4(CC4)c4ccc(F)cc43)nc3cc(Cl)ccc32)CC1]

Ethanesulfonylchloride (23.4 µL, 0.247 mmol) was added to a cooled (0° C.) solution of compound 29 (60 mg, 0.140 mmol) and NEt₃ (34.5 µL, 0.248 mmol) in anhydrous CH₂Cl₂ (2.5 mL) under N₂ and stirred at rt for 19 h. The reaction was diluted with CH₂Cl₂ (20 mL), washed with saturated aqueous NH₄Cl solution, water (2×) and brine (10 mL each), dried (MgSO₄) and the solvent removed under reduced pressure.

Purification by flash chromatography (30-100% EtOAc in heptane) afforded an off-white solid (73 mg, 79%). ¹H NMR (400 MHz, CDCl₃): δ 7.79 (d, J=2.0 Hz, 1H), 7.46 (d, J=8.8 Hz, 1H), 7.34-7.30 (m, 1H), 7.23 (dd, J=8.7, 2.0 Hz, 1H), 6.74-6.67 (m, 2H), 5.28 (s, 2H), 4.94-4.85 (m, 1H), 4.02-3.95 (m, 2H), 3.06-2.93 (m, 4H), 2.55-2.44 (m, 2H), 1.74-1.67 (m, 4H), 1.57-1.53 (m, 2H), 1.41 (t, J=7.4 Hz, 3H). LRMS (APCI+) m/z 516.8 [M+H]⁺

36: 1'-({5-Chloro-1-[1-(2-methanesulfonylethyl)piperidin-4-yl]-1H-1,3-benzodiazol-2-yl}methyl)-6'-fluoro-1',2'-dihydrospiro[cyclopropane-1,3'-indole]-2'-one

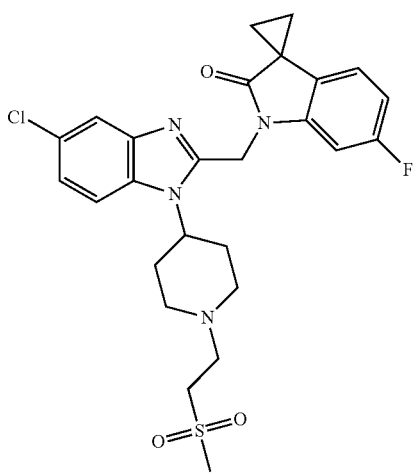 [SMILES: CS(=O)(=O)CCN1CCC(n2c(CN3C(=O)C4(CC4)c4ccc(F)cc43)nc3cc(Cl)ccc32)CC1]

Methyl vinyl sulfone (21.2 µL, 0.240 mmol) was added to a cooled (0° C.) solution of compound 29 (76 mg, 0.179 mmol) in anhydrous THF (2.5 mL) under N₂ and stirred at rt for 22 h. Extra methyl vinyl sulfone (7.8 µL, 0.89 mmol) was added and the reaction stirred for a further 1.5 h. The volatiles were evaporated under reduced pressure, and the crude residue was purified directly by flash chromatography (30-100% EtOAc in heptane) to afford the product as a pale brown solid (54 mg, 57%). ¹H NMR (400 MHz, DMSO-d₆): δ 7.73 (d, J=2.1 Hz, 1H), 7.62 (d, J=8.7 Hz, 1H), 7.24 (dd, J=8.8, 2.1 Hz, 1H), 7.11-7.04 (m, 2H), 6.84-6.81 (m, 1H), 5.36 (s, 2H), 4.58-4.48 (m, 1H), 3.10-3.02 (m, 5H), 2.78 (t, J=6.8 Hz, 2H), 2.35-2.24 (m, 3H), 2.17-2.08 (m, 2H), 1.77-1.67 (m, 4H), 1.60-1.55 (m, 2H). LRMS (APCI+) m/z 531.1 [M+H]⁺

Example 37: Efficacy in vitro

Compounds were subjected to RSV fusion assays and plaque reduction assays according to the following protocols.

RSV Fusion Assay

HEK 293T ((ECACC 12022001) cells were cultured in T75 culture flasks in Dulbecco's medium (DMEM) containing 10% Foetal Bovine serum (FBS), 50 units per mL Penicillin and 50 µg/mL Streptomycin and warmed to 37° C. prior to use. The cells were passaged by first washing briefly with 5 mL Phosphate buffered saline (PBS), followed by addition of 2 mL of Trypsin Ethylenediaminetetraacetic acid (EDTA) to detach the cells. Once cells had detached from the flask, 8 mL media was then added to and the cells dispersed via pipetting against the bottom of the flask.

The cells were counted and diluted to 3×10⁵ cells/ml in fresh media. Two T75 flasks were each seeded with 15.6 mL diluted cells, cells were also subcultured at a ratio of between 1:2 and 1:10, to continue the stock. The flasks were then incubated for 24 h at 37° C. and 5% CO₂.

The plasmid DNA (for pFR-Luc and pcDNA3. 1_Gal4/NFKB) to be transfected into the HEK 293T cells was first prepared in serum free media (Opti-MEM, Invitrogen), containing the transfection reagent FuGENE® 6 (Promega). Serum free media was placed in a 1.5 mL eppendorf tube then the FuGENE 6 was added into the media. The tube was vortexed for 1 s before being incubated at RT for 5 min. 7.79 ng of both pFR_luc and pCDNA3.1_A2_F plasmid DNA were added to tube 1 and 7.79 ng of pCDNA3.1_GAL4-NF-κB plasmid to tube 2. The tubes were vortexed for 1 second and then incubated at room temperature for 15 min. Each transfection mixture was then added into the media of one of the T75 flasks of 293T cells. Cells were cultured for 24h at 37° C., 5% CO₂ in a humidified incubator.

Compounds were diluted (in a polypropylene round-bottomed 96 well plate) 1:3 in a twelve point dilution curve to give top [final] of either 25 µM, 3 µM, 1 µM or 500 nM. A control compound was included in every assay at a top concentration of 3 µM. Transfected cells were counted and diluted to 4×10⁵ cells/mL in fresh media. 50 µL of transfection population 1 were added to all wells of the 96 well flat bottom white opaque assay plates. 100 µL diluted compound (2 rows per compound), control compound (one row) and controls (DMSO (0% inhibition, four wells), 3 µM positive control (100% inhibition, four wells) and media (transfection population 1 only, four wells) were added to the appropriate wells. 50 µL of the diluted (4×10⁵ cells/mL) population 2 cells when then added to all wells, except the four wells of transfection population 1 only where an extra 50 µL of this cells population was added.

The plates were then incubated for 24 h at 37° C. and 5% CO$_2$. After this time, 100 µL was removed from all wells and 60 µL of ONE-Glo™ (Promega) reagent, pre-equilibrated to room temperature, was added. Plates were then incubated for 3 min at room temperature before luminescence was read, using the ONE-Glo protocol, on the GloMax Explorer System (Promega) multimode reader. Analysis was carried out in Dotmatics software. All raw data were background subtracted (subtraction of mean 3 µM positive control value), before IC$_{50}$ calculation.

Plaque Reduction Assay:

HEp-2 cells (ATCC, CCL23) were passaged in flasks and seeded in 96-well plates in DMEM containing antibiotics and supplemented with 10% FBS. During inoculation and subsequent incubation, cells were cultured in DMEM containing 3% FBS. 100 plaque forming unit (PFU)/well of RSV (RSV A2 VR-1540) was mixed with ten serial dilutions of compound. Subsequently, 100 µL of the virus/compound mixtures was added to confluent HEp-2 cell monolayers. The cells and virus/compound mixtures were incubated at 35° C. in a humidified 5% CO$_2$ incubator for 1 day.

Cells were washed twice with PBS before adding 50% v/v EtOH/MeOH, and then stored at −20° C. On the day of the staining, fixative was first removed from the plates. Plates were washed 3× with PBS. A pre-titrated amount of the primary antibody was added in 60 µL PBS/2% milk powder, and plates incubated for 1 h at it. The plates were washed 3× with PBS/0.05% Tween20 before addition of goat anti-mouse horse radish peroxidase in 60 µL PBS/2% milk powder, and incubated for 1 h at rt. Following three wash steps with PBS/0.05% Tween20, 60 µL ready-to-use True-Blue was added and plates were incubated at rt for 10-15 min before adding MilliQ water. Plates were washed once with water, incubated for 30-60 min and after removal of water, air-dried in the dark.

Plates were scanned and analyzed using the Immunospot S6 UV analyzer, which is equipped with BioSpot analysis software for counting immunostained plaques (virospots). Plaque counts were used to calculate % infection relative to the mean of the spot count (SC) in the virus control wells for RSV. IC$_{50}$/IC$_{90}$ values were calculated as 50% or 90% reduction in signal, respectively, by interpolation of inhibition curves fitted with a 4-parameter nonlinear regression with a variable slope in GraphPad 5.0 (Prism).

Results

| Compound | RSV Fusion Assay (n ≥ 2) IC$_{50}$ (nM)* | RSV Plaque Reduction Assay Strain A2 (n = 1) | |
|---|---|---|---|
| | | IC$_{50}$ (nM) | IC$_{90}$ (nM) |
| 14 | 18 | 3.5 | 34 |
| 20 | 12 | 5.9 | 7.5 |
| 33 | 3.3 | 0.49 | 4.4 |
| 35 | 5.0 | 0.87 | 5.2 |
| 13 | 10 | 4.5 | 41 |
| 11 | 24 | 5 | 41 |
| 9 | 15 | 4.2 | 28 |
| 10 | 12 | 2.5 | 31 |
| 1 | 19 | 5.9 | 50 |
| 18 | 70 | 7.6 | 60 |
| 12 | 71 | 29 | 200 |
| 28 | 115 | 9.5 | 48 |

*The given IC$_{50}$ represents the average of at least 2 independent experiments Example 38: In vitro Pharmacokinetics Compounds were subjected to the following assays to investigate liver microsomal stability and permeability.

Microsomal Incubation: Experimental Procedure

Pooled liver microsomes are purchased from a reputable commercial supplier and stored at −80° C. prior to use.

Microsomes (final protein concentration 0.5 mg/mL), 0.1 M phosphate buffer pH 7.4 and test compound (final substrate concentration 3 µM; final DMSO concentration 0.25%) are pre-incubated at 37° C. prior to the addition of NADPH (final concentration 1 mM) to initiate the reaction. The final incubation volume is 50 uL. A control incubation is included for each compound tested where 0.1 M phosphate buffer pH 7.4 is added instead of NADPH (minus NADPH). Two control compounds are included with each species. All incubations are performed singularly for each test compound.

Each compound is incubated for 0, 5, 15, 30 and 45 min. The control (minus NADPH) is incubated for 45 min only. The reactions are stopped by transferring 20 µL of incubate to 60 µL MeOH at the appropriate time points. The termination plates are centrifuged at 2,500 rpm for 20 min at 4° C. to precipitate the protein.

Following protein precipitation, the sample supernatants are combined in cassettes of up to 4 compounds, internal standard is added and samples analysed by LC-MS/MS. From a plot of ln peak area ratio (compound peak area/ internal standard peak area) against time, the gradient of the line is determined. Subsequently, half-life and intrinsic clearance are calculated.

MDR1-MDCK Permeability: Experimental Procedure

MDR1-MDCK cells obtained from the NIH (Rockville, Md., USA) are used between passage numbers 6-30. Cells are seeded onto Millipore Multiscreen Transwell plates at 3.4×10$^5$ cells/cm$^2$. The cells are cultured in DMEM and media is changed on day 3. On day 4 the permeability study is performed. Cell culture and assay incubations are carried out at 37° C. in an atmosphere of 5% CO$_2$ with a relative humidity of 95%. On the day of the assay, the monolayers are prepared by rinsing both basolateral and apical surfaces twice with Hanks Balanced Salt Solution (HBSS) at the desired pH warmed to 37° C. Cells are then incubated with HBSS at the desired pH in both apical and basolateral compartments for 40 min to stabilise physiological parameters.

The dosing solutions are prepared by diluting test compound with assay buffer to give a final test compound concentration of 10 µM (final DMSO concentration of 1% v/v). The fluorescent integrity marker lucifer yellow is also included in the dosing solution. Analytical standards are prepared from test compound DMSO dilutions and transferred to buffer, maintaining a 1% v/v DMSO concentration.

For assessment of A-B permeability, HBSS is removed from the apical compartment and replaced with test compound dosing solution. The apical compartment insert is then placed into a companion plate containing fresh buffer (containing 1% v/v DMSO). For assessment of B-A permeability, FIBSS is removed from the companion plate and replaced with test compound dosing solution. Fresh buffer (containing 1% v/v DMSO) is added to the apical compartment insert, which is then placed into the companion plate. At 60 min the apical compartment inserts and the companion plates are separated and apical and basolateral samples diluted for analysis. Test compound permeability is assessed in duplicate. Compounds of known permeability characteristics are run as controls on each assay plate.

Test and control compounds are quantified by LC-MSMIS cassette analysis using an 8-point calibration with appropriate dilution of the samples. The starting concentration (C$_0$) is determined from the dosing solution and the experimental recovery calculated from $C_0$ and both apical and basolateral compartment concentrations. The integrity of the monolayer throughout the experiment is checked by monitoring lucifer yellow permeation using fluorimetric analysis. Lucifer yellow permeation is high if monolayers have been damaged.

Results

| Pharmacokinetic property | Value |
| --- | --- |
| Liver Microsoinal Stability [$t_{1/2}$ (min); rat/dog/human] | Compound 33: 14.8/186/486 Compound 35: 5.5/166/34.6 |
| Permeability MDR1-MDCK $P_{app}$ ($10^{-6}$ cms$^{-1}$) A-B/B-A | Compound 14: 4.8/68 Compound 20: 1.6/61.3 Compound 33: 12.4/35.5 Compound 35: 12.7/22.8 |

Example 39: Cytochrome P450 inhibition

Compounds of the invention were tested for inhibition of Cytochrome P450 enzymes.

Test compound (0.1, 0.25, 1, 2.5, 10, 25 µM in DMSO; final DMSO concentration 0.3%) was incubated with human liver microsomes (0.25 mg/mL) and NADPH (1 mM) in the presence of a cytochrome P450 isoform-specific probe substrate. The metabolites were monitored by LC-MS/MS and a decrease in the formation of the metabolite compared to the vehicle control used to calculate an IC$_{50}$ value (test compound concentration which produces 50% inhibition). A cytochrome P450 isoform-specific selective inhibitor was screened alongside the test compounds as a positive control. Results for Compound 33:

| Isoform (substrate) | Cytochrome P450 inhibition IC$_{50}$ (µM) Compound 33 |
| --- | --- |
| CYP1A2 | >25 |
| CYP2B6 | >25 |
| CYP2C8 | >25 |
| CYP2C9 | >25 |
| CYP2C19 | >25 |
| CYP2D6 | >25 |
| CYP3A4 * | 0.674 |
| CYP3A4 † | 3.94 |

Notes:
* substrate = midazolam.
† substrate = testosterone.

Example 40: In Vivo Pharmacokinetics

The pharmacokinetics of compounds of the invention were studied in vivo in the dog at doses of 3 mg/kg (PO).

Methods

Beagle dogs (n=3) were treated with experimental compounds via oral administration (3 mg/kg). Oral administration was performed by gavage at a dose of 3 mg/kg at a concentration of 0.6 mg/mL in % dimethylacetamide, 30% PEG 400 & 65% (2-hydroxypropyl)-β-cyclodextrin solution (20% w/v aq.). Serial blood samples were collected at 0.08, 0.25, 0.5, 1, 2, 4, 6, 8, 12 and 24 hours post dosing of compound. Animals were observed for any overt clinical signs or symptoms. Serial plasma samples were taken at the defined time points and stored immediately at −80° C.

Following protein precipitation with acetonitrile, samples were analysed with tandem. liquid chromatography/mass spectrometry using electrospray ionisation. A full matrix curve with internal standards was employed and PK parameters were calculated.

Results
Compound 33:

| Pharmacokinetic Property | Value |
| --- | --- |
| $t_{1/2}$ (hr) | 7.24 |
| $T_{max}$ (hr) | 0.67 |
| $C_{max}$ (ng/mL) | 535.40 |
| AUC$_{last}$ (hr*ng/mL) | 3874.91 |
| AUC$_{all}$ (hr*ng/mL) | 3874.91 |
| AUC$_{inf}$ (hr*ng/mL) | 4282.46 |

Example 41: Aqueous Formulation

The compound of Example 1 is formulated as a solution in 30% w/v captisol (i.e. sulfobutylether-beta-cyclodextrin) at pH4 according to the following procedure.

A carrier of 30% w/v captisol (i.e. sulfobutylether-beta-cyclodextrin) is prepared by weighing the required amount of captisol into a suitable vessel, adding approximately 80% of the final volume of water and magnetically stirring until a solution is formed. The carrier is then made up to volume with water.

An aqueous solution of a compound of Example 1 is prepared by weighing 175 mg of the compound into a suitable vessel and adding approximately 80% of the required volume of the carrier. Using an aqueous solution of hydrochloric acid, the pH is adjusted to pH2 and the resulting mixture is magnetically stirred until a solution is formed. The formulation is then made up to volume with carrier and the pH is adjusted to pH4 using an aqueous solution of sodium hydroxide.

Example 42: Tablet Composition

Tablets, each weighing 0.15 g and containing 25 mg of a compound of the invention are manufactured as follows:
Composition for 10,000 tablets
Compound of the invention (250 g)
Lactose (800 g)
Corn starch (415 g)
Talc powder (30 g)
Magnesium stearate (5 g)

The compound of the invention, lactose and half of the corn starch are mixed. The mixture is then forced through a sieve 0.5 mm mesh size. Corn starch (10 g) is suspended in warm water (90 mL). The resulting paste is used to granulate the powder. The granulate is dried and broken up into small fragments on a sieve of 1.4 mm mesh size. The remaining quantity of starch, talc and magnesium is added, carefully mixed and processed into tablets.

Example 43: Injectable Formulation

| Compound of the invention | 200 mg |
| --- | --- |
| Hydrochloric Acid Solution 0.1M or Sodium Hydroxide Solution 0.1M q.s. to pH | 4.0 to 7.0 |
| Sterile water q.s. to | 10 mL |

The compound of the invention is dissolved in most of the water (35° C.-40° C.) and the pH adjusted to between 4.0 and 7.0 with the hydrochloric acid or the sodium hydroxide as appropriate. The batch is then made up to volume with water and filtered through a sterile micropore filter into a sterile 10 mL amber glass vial (type 1) and sealed with sterile closures and overseals.

Example 44: Intramuscular Injection

| Compound of the invention | 200 mg |
| Benzyl Alcohol | 0.10 g |
| Glycofurol 75 | 1.45 g |
| Water for injection q.s to | 3.00 ml |

The compound of the invention is dissolved in the glycofurol. The benzyl alcohol is then added and dissolved, and water added to 3 mL. The mixture is then filtered through a sterile micropore filter and sealed in sterile 3 mL glass vials (type 1).

Example 45: Syrup Formulation

| Compound of invention | 250 mg |
| Sorbitol Solution | 1.50 g |
| Glycerol | 2.00 g |
| Sodium benzoate | 0.005 g |
| Flavour | 0.0125 mL |
| Purified Water q.s. to | 5.00 mL |

The compound of the invention is dissolved in a mixture of the glycerol and most of the purified water. An aqueous solution of the sodium benzoate is then added to the solution, followed by addition of the sorbitol solution and finally the flavour. The volume is made up with purified water and mixed well.

The invention claimed is:

1. A compound which is a benzimidazole derivative of formula (I):

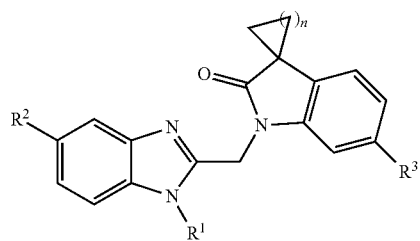

wherein:

$R^1$ is —$(CH_2)_m$—$R^4$ or

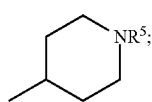

$R^2$ is halo, —$(CH_2)_m$—$NH_2$ or —$(CH_2)_n$—C(=NH)—$NH_2$;

$R^3$ is H or F;

$R^4$ is —NH—$(CH_2)_2$—$(NH)_r$—$R^5$, —NH—$(CHR^5R^6)$ or a group of the following formula (A):

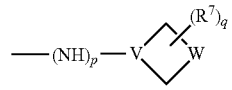

W is —$(CH_2)_m$—, —$CH_2$—O—$CH_2$—, —$CH_2$—S—$CH_2$—, —$(CH_2)_r$—S(O)$_2$—$CH_2$— or —$(CH_2)_r$—$NR^5$—$CH_2$—;

m is an integer of 1 to 3;

n is 1 or 2;

p is 1 and V is CH; or p is 0 and V is N;

q is 0 or 1;

r is 0 or 1;

$R^5$ is H, —$SO_2Me$, —$SO_2Et$, —$SO_2CF_3$, —COMe, —$CONMe_2$, —$CONH_2$ or —$CH_2CH_2SO_2Me$;

$R^6$ is H or $C_1$-$C_6$ alkyl; and $R^7$ is —$SO_2Me$, —$SO_2Et$, —$SO_2CF_3$, —COMe, —$CONMe_2$, —$CONH_2$ or —$CH_2CH_2SO_2Me$;

or a pharmaceutically acceptable salt thereof.

2. A compound according to claim 1 wherein $R^1$ is —$(CH_2)_m$—$R^4$ in which m is 2 or 3 and $R^4$ is selected from:
  (i) —NH—$(CH_2)_2$—$(NH)_r$—$R^5$ wherein r is 0 or 1 and $R^5$ is selected from —$SO_2Me$, —$SO_2Et$ and —$SO_2CF_3$;
  (ii) —NH—$(CHR^5R^6)$ wherein $R^5$ is —$CONH_2$ or —$CONMe_2$ and $R^6$ is $C_1$-$C_6$ alkyl;
  (iii) —$(CH_2)_m$—$R^4$ in which m is 2 or 3 and $R^4$ is a group of formula (A) in which p is 1, q is 0, V is CH and W is —$(CH_2)_r$—S(O)$_2$—$CH_2$—or —$(CH_2)_r$—$NR^5$—$CH_2$-in which r is 0 and $R^5$ is $SO_2Me$ or —$SO_2Et$;
  (iv) —$(CH_2)_m$—$R^4$ in which m is 2 or 3 and $R^4$ is a group of formula (A) in which p is 0, V is N, W is —$(CH_2)_m$—in which m is an integer of 1 to 3, q is 1 and $R^7$ is —$SO_2Me$, —$SO_2Et$, —$CONH_2$ or —$CON Me_2$; and
  (v) —$(CH_2)_m$—$R^4$ in which m is 2 or 3 and $R^4$ is a group of formula (A) in which p is 0, V is N, q is 0 and W is —$CH_2$—O—$CH_2$—, —$CH_2$—S—$CH_2$—, —$(CH_2)_r$—S(O)$_2$—$CH_2$— or —$(CH_2)_r$—$NR^5$—$CH_2$- in which r is 0 or 1 and $R^5$ is —$SO_2Me$, —$SO_2Et$ or —COMe.

3. A compound according to claim 1 wherein:

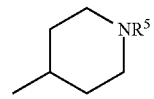

$R^1$ is in which $R^5$ is H, —$SO_2Me$, —$SO_2Et$, —COMe, —$CONMe_2$ or —$CH_2CH_2SO_2Me$.

4. A compound according to claim 1 wherein $R^2$ is F, Cl or —$CH_2$—$NH_2$.

5. A compound according to claim 1 wherein the group of formula (A) is selected from the following structures:

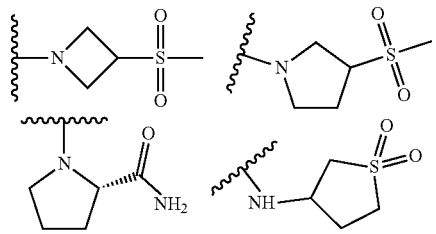

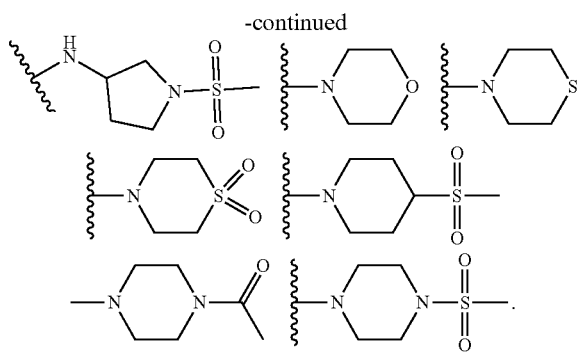

6. A compound according to claim 1 which is selected from:
  1'-({5-Chloro-1-[3-(4-methanesulfonylpiperazin-1-yl)propyl]-1H-1,3-benzodiazol-2-yl}methyl)-6'-fluoro-1',2'-dihydrospiro[cyclopropane-1,3'-indole]-2'-one;
  1'-[(5-chloro-1-{2-[(2-methanesulfonylethyl)amino]ethyl}-1H-1,3-benzodiazol-2-yl)methyl]-6'-fluoro-1',2'-dihydrospiro[cyclopropane-1,3'-indole]-2'-one;
  N-[2-({2-[5-chloro-2-({6'-fluoro-2'-oxo-1',2'-dihydrospiro[cyclopropane-1,3'-indole]-1'-yl}methyl)-1H-1,3-benzodiazol-1-yl]ethyl}amino)ethyl]1,1,1-trifluoromethanesulfonamide;
  3-({2-[5-chloro-2-({6'-fluoro-2'-oxo-1',2'-dihydrospiro[cyclopropane-1,3'-indole]-1'-yl}methyl)-1H-1,3-benzodiazol-1-yl]ethyl}amino)-1λ6-thiolane-1,1-dione;
  1'-[(5-chloro-1-{2-[(1-methanesulfonylpyrrolidin-3-yl)amino]ethyl}-1H-1,3-benzodiazol-2-yl)methyl]-6'-fluoro-1',2'-dihydrospiro[cyclopropane-1,3'-indole]-2'-one;
  1-{2-[5-chloro-2-({6'-fluoro-2'-oxo-1',2'-dihydrospiro[cyclopropane-1,3'-indole]-1'-yl}methyl)-1H-1,3-benzodiazol-1-yl]ethyl}pyrrolidine-2-carboxamide;
  1'-({5-chloro-1-[2-(3-methanesulfonylpyrrolidin-1-yl)ethyl]-1H-1,3-benzodiazol-2-yl}methyl)6'-fluoro-1',2'-dihydrospiro[cyclopropane-1,3'-indole]-2'-one;
  1-({5-chloro-1-[2-(4-methanesulfonylpiperidin-1-yl)ethyl]-1H-1,3-benzodiazol-2-yl}methyl)-6'-fluoro-1',2'-dihydrospiro[cyclopropane-1,3'-indole]-2'-one;
  1-({5-chloro-1-[2-(4-methanesulfonylpiperazin-1-yl)ethyl]-1H-1,3-benzodiazol-2-yl}methyl)-6'fluoro-1',2'-dihydrospiro[cyclopropan-1,3'-indole]-2'-one;
  1'-[(5-Chloro-1-{3-[(2-methanesulfonylethy)amino]propyl}-1H-1,3-benzodiazol-2-yl)methyl]-6'-fluoro-1',2'-dihydrospiro[cyclopropane-1,3'-indole]-2'-one;
  1'-{[5-Chloro-1-(3-{[2-(ethanesulfonyl)ethyl]amino}propyl)-1H-1,3-benzodiazol-2-yl]methyl}-6'fluoro-1',2'-dihydrospiro[cyclopropane-1,3'-indole]-2'-one;
  (2S)-2-({3-[5-chloro-2-({6'-fluoro-2'-oxo-1',2'-dihydrospiro[cyclopropane-1,3'-indole]-1'-yl}methyl)-1H-1,3-benzodiazol-1-yl]propyl}amino)-3-methylbutanamide;
  1-({5-Chloro-1-[3-(3-methanesulfonylazetidin-1-yl)propyl]-1H-1,3-benzodiazol-2-yl}methyl)-6'fluoro-1',2'-dihydrospiro[cyclopropane-1,3'-indole]-2'-one;
  1-({5-Chloro-1-[3-(3-methanesulfonylpyrrolidin-1-yl)propyl]-1H-1,3-benzodiazol-2-yl}methyl)-6'-fluoro-1',2'-dihydrospiro[cyclopropane-1,3'-indole]-2'-one;
  (2S)-1-{3-[5-chloro-2-({6'-fluoro-2'-oxo-1',2'-dihydrospiro[cyclopropane-1,3'-indole]-1'-yl}methyl)-1H-1,3-benzodiazol-1-yl]propyl}pyrrolidine-2-carboxamide;
  3-({3-[5-Chloro-2-({6'-fluoro-2'-oxo-1',2'-dihydrospiro[cyclopropane-1,3'-indole]-1'-yl}methyl)-1H-1,3-benzodiazol-1-yl]propyl}amino)-1λ6-thiolane-1,1-dione;
  1'-[(5-Chloro-1-{3-[(1-methanesulfonylpyrrolidin-3-yl)amino]propyl}-1H-1,3-benzodiazol-2-yl)methyl]-6'-fluoro-1',2'-dihydrospiro[cyclopropane-1,3'-indole]-2'-one;
  1'-({5-Chloro-1-[3-(morpholin-4-yl)propyl]-1H-1,3-benzodiazol-2-yl}methyl)-6'-fluoro-1',2'-dihydrospiro[cyclopropane-1,3'-indole]-2'-one;
  1'-({5-Chloro-1-[3-(thiomorpholin-4-yl)propyl]-1H-1,3-benzodiazol-2-yl}methyl)-6'-fluoro-1',2'-dihydrospiro[cyclopropane-1,3'-indole]-2'-one;
  4-{3-[5-Chloro-2-({6'-fluoro-2'-oxo-1',2'-dihydrospiro[cyclopropane-1,3'-indole]-1'-yl}methyl)-1H-1,3-benzodiazol-1-yl]propyl}-1λ6-thiomorpholine-1,1-dione;
  1-({5-Chloro-1-[3-(4-methanesulfonylpiperidin-1-yl)propyl]-1H-1,3-benzodiazol-2-yl}methyl)-6'-fluoro-1',2'-dihydrospiro[cyclopropane-1,3'-indole]-2'-one;
  1'-({1-[3-(4-Acetylpiperazin-1-yl)propyl]-5-chloro-1H-1,3-benzodiazol-2-yl}methyl)-6'-fluoro-1',2'-dihydrospiro[cyclopropane-1,3'-indole]-2'-one;
  6'-Fluoro-1'-[(5-fluoro-1-{3-[(2-methanesulfonylethy)amino]propyl}-1H-1,3-benzodiazol-2-yl)methyl]-1'2'-dihydrospiro[cyclopropane-1,3'-indole]-2'-one;
  (2S)-2-(({3-[5-Fluoro-2-({6'-fluoro-2'-oxo-1',2'-dihydrospiro[cyclopropane-1,3'-indole]-1'-yl}methyl-1H-1,3-benzodiazol-1-yl]propyl}amino)-3-methylbutanamide;
  (2S)-1-({3-[5-fluoro-2-({6'-fluoro-2'-oxo-1',2'-dihydrospiro[cyclopropane-1,3'-indole]-1'-yl}methyl)-1H-1,3-benzodiazol-1-yl]propyl}pyrrolidine-2-carboxamide;
  6'-Fluoro-1'-({5-fluoro-1-[3-(morpholin-4-yl)propyl]-1H-1,3-benzodiazol-2-yl}methyl)-1',2'-dihydrospiro[cyclopropane-1,3'-indole]-2'-one;
  1'-({1-[3-(4-Acetylpiperazin-1-yl)propyl]-5-fluoro-1H-1,3-benzodiazol-2-yl}methyl)-6'-fluoro-1',2'-dihydrospiro[cyclopropane-1,3'-indole]-2'-one;
  6'-Fluoro-1'-({5-fluoro-1-[3-(4-methanesulfonylpiperazin-1-yl)propyl]-1H-1,3-benzodiazol-2-yl}methyl)-1',2'-dihydrospiro[cyclopropane-1,3'-indole]-2'-one;
  1'-{[5-Chloro-1-(piperidin-4-yl)-1H-1,3-benzodiazol-2-yl]methyl}-6'-fluoro-1',2'-dihydrospiro[cyclopropane-1,3'-indole]-2'-one;
  1'-{[5-Chloro-1-(piperidin-4-yl)-1H-1,3-benzodiazol-2-yl]methyl}-6'-fluoro-1',2'-dihydrospiro[cyclobutane-1,3'-indole]-2'-one;
  1'-{[1-(1-Acetylpiperidin-4-yl)-5-chloro-1H-1,3-benzodiazol-2-yl]methyl}-6'-fluoro-1',2'-dihydrospiro[cyclopropane-1,3'-indole]-2'-one;
  4-[5-Chloro-2-({6'-fluoro-2'-oxo-1',2'-dihydrospiro[cyclopropane-1,3'-indole]-1'-yl}methyl)-1H-1,3-benzodiazol-1-yl]-N,N-dimethylpiperidine-1-carboxamide;
  1'-{[5-Chloro-1-(1-methanesulfonylpiperidin-4-yl)-1H-1,3-benzodiazol-2-yl]methyl}-6'-fluoro-1',2'-dihydrospiro[cyclopropane-1,3'-indole]-2'-one;
  1'-{[5-Chloro-1-(1-methanesulfonylpiperidin-4-yl)-1H-1,3-benzodiazol-2-yl]methyl}-6'-fluoro-1',2'-dihydrospiro[cyclobutane-1,3'-indole]-2'-one;
  1'-({5-Chloro-1-[1-(ethanesulfonyl)piperidin-4-yl]-1H-1,3-benzodiazol-2-yl}methyl)-6'-fluoro-1',2'-dihydrospiro[cyclopropane-1,3'-indole]-2'-one;
  1'-({5-Chloro-1-[1-(2-methanesulfonylethyl)piperidin-4-yl]-1H-1,3-benzodiazol-2-yl}methyl)-6'fluoro-1',2'-dihydrospiro[cyclopropane-1,3'-indole]-2'-one;
and the pharmaceutically acceptable salts thereof.

7. A pharmaceutical composition which comprises a compound as defined in claim 1 and a pharmaceutically acceptable carrier or diluent.

8. A method of treating a subject suffering from or susceptible to an RSV infection, which method comprises administering to said subject an effective amount of a compound as defined in claim 1.

9. A pharmaceutical composition which comprises (a) a compound as defined in claim 1, and (b) one or more further therapeutic agents, together with a pharmaceutically acceptable carrier or diluent, wherein the further therapeutic agent is selected from the group consisting of:
  (i) a RSV nucleocapsid(N)-protein inhibitor;
  (ii) another protein inhibitor, such as one that inhibits the phosphoprotein (P) protein and/or large (L) protein;
  (iii) an anti-RSV monoclonal antibody, such as an F-protein antibody;
  (iv) an immunomodulating toll-like receptor compound;
  (v) another respiratory virus anti-viral, such as an anti-influenza and/or anti-rhinovirus compound; and
  (vi) an anti-inflammatory compound.

10. A process for producing a pharmaceutically acceptable salt as defined in claim 1, which process comprises treating a pyrimidine of formula (I) as defined in claim 1 with a suitable acid in a suitable solvent.

11. A process according to claim 10, wherein the acid is selected from hydrochloric acid, hydrobromic acid, hydroiodic acid, sulphuric acid, nitric acid, phosphoric acid, methanesulfonic acid, benzenesulphonic acid, formic acid, acetic acid, trifluoroacetic acid, propionic acid, oxalic acid, malonic acid, succinic acid, fumaric acid, maleic acid, lactic acid, malic acid, tartaric acid, citric acid, ethanesulfonic acid, aspartic acid and glutamic acid.

12. A method according to claim 8, which method further comprises administering to the subject a further therapeutic agent selected from the group consisting of:
  (i) a RSV nucleocapsid(N)-protein inhibitor;
  (ii) another protein inhibitor, such as one that inhibits the phosphoprotein (P) protein and/or large (L) protein;
  (iii) an anti-RSV monoclonal antibody, such as an F-protein antibody;
  (iv) an immunomodulating toll-like receptor compound;
  (v) another respiratory virus anti-viral, such as an anti-influenza and/or anti-rhinovirus compound; and
  (vi) an anti-inflammatory compound.

* * * * *